United States Patent
Barnett et al.

(10) Patent No.: US 10,905,123 B2
(45) Date of Patent: Feb. 2, 2021

(54) HERBICIDAL COMPOUNDS

(71) Applicant: Syngenta Participations AG, Basel (CH)

(72) Inventors: Susan Patricia Barnett, Bracknell (GB); Neil Brian Carter, Bracknell (GB); Alison Clare Elliott, Bracknell (GB); Derek McCormack, Bracknell (GB); Matthew Murdoch Woodhead McLachlan, Bracknell (GB); James Alan Morris, Bracknell (GB); Anne Mary Seville, Bracknell (GB); Matthew John Webber, Bracknell (GB)

(73) Assignee: Syngenta Participations AG, Basel (CH)

( * ) Notice: Subject to any disclaimer, the term of this patent is extended or adjusted under 35 U.S.C. 154(b) by 172 days.

(21) Appl. No.: 15/549,707

(22) PCT Filed: Feb. 3, 2016

(86) PCT No.: PCT/EP2016/052232
§ 371 (c)(1),
(2) Date: Aug. 9, 2017

(87) PCT Pub. No.: WO2016/128266
PCT Pub. Date: Aug. 18, 2016

(65) Prior Publication Data
US 2018/0027815 A1    Feb. 1, 2018

(30) Foreign Application Priority Data
Feb. 10, 2015    (GB) .................. 1502164.5

(51) Int. Cl.
| | |
|---|---|
| *A01N 47/18* | (2006.01) |
| *A01N 43/56* | (2006.01) |
| *A01N 43/72* | (2006.01) |
| *A01N 47/36* | (2006.01) |
| *A01N 43/78* | (2006.01) |
| *A01N 47/20* | (2006.01) |
| *A01N 43/76* | (2006.01) |
| *A01N 43/80* | (2006.01) |
| *C07D 417/14* | (2006.01) |
| *C07D 413/14* | (2006.01) |
| *A01N 47/22* | (2006.01) |
| *C07D 401/04* | (2006.01) |
| *C07D 403/04* | (2006.01) |
| *A01N 43/46* | (2006.01) |

(52) U.S. Cl.
CPC ............ *A01N 47/18* (2013.01); *A01N 43/56* (2013.01); *A01N 43/72* (2013.01); *A01N 43/76* (2013.01); *A01N 43/78* (2013.01); *A01N 43/80* (2013.01); *A01N 47/20* (2013.01); *A01N 47/22* (2013.01); *A01N 47/36* (2013.01); *C07D 401/04* (2013.01); *C07D 403/04* (2013.01); *C07D 413/14* (2013.01); *C07D 417/14* (2013.01); *A01N 43/46* (2013.01); *A01N 2300/00* (2013.01)

(58) Field of Classification Search
CPC ........ A01N 47/18; A01N 47/22; A01N 43/56; A01N 43/72; A01N 47/36; A01N 47/20; A01N 43/80; A01N 43/78; A01N 43/76; A01N 43/46; A01N 2300/00; C07D 401/04; C07D 403/04; C07D 413/14; C07D 417/14
See application file for complete search history.

(56) References Cited

U.S. PATENT DOCUMENTS

2014/0213448 A1    7/2014    Buysse et al.

FOREIGN PATENT DOCUMENTS

| JP | 2014111559 | 6/2014 |
|---|---|---|
| WO | 2012/061288 A1 | 10/2012 |
| WO | 2012/061290 A2 | 10/2012 |
| WO | 2013/062981 A1 | 5/2013 |
| WO | 2013/162715 A1 | 10/2013 |

OTHER PUBLICATIONS

International Search Report for International Patent Application No. PCT/EP2016/052232 dated Mar. 16, 2016.
GB Search Report for Patent Application No. GB1502164.5 dated Aug. 10, 2015.

*Primary Examiner* — John Pak
*Assistant Examiner* — Andriae M Holt
(74) *Attorney, Agent, or Firm* — Baker & Hostetler LLP; Toni-Junell Herbert

(57) ABSTRACT

The present invention relates to herbicidally-active pyridino-/pyrimidino-pyrazole derivatives, as well as to processes and intermediates used for the preparation of such derivatives. The invention further extends to herbicidal compositions comprising such derivatives, as well as to the use of such compounds and compositions in controlling undesirable plant growth: in particular the use in controlling weeds, in crops of useful plants.

21 Claims, No Drawings

HERBICIDAL COMPOUNDS

RELATED APPLICATION INFORMATION

This application is a 371 of International Application No. PCT/EP2016/052232, filed Feb. 3, 2016, which claims priority to GB Application No. 1502164.5, filed Feb. 10, 2015, the contents of which are incorporated herein by reference herein.

The present invention relates to herbicidally-active pyridino-/pyrimidino-pyrazole derivatives, as well as to processes and intermediates used for the preparation of such derivatives. The invention further extends to herbicidal compositions comprising such derivatives, as well as to the use of such compounds and compositions in controlling undesirable plant growth: in particular the use in controlling weeds, in crops of useful plants.

Herbicidal pyrimidino-imidazoles are known from WO2005/047281. Pyridino-/pyrimidino-pyrazole derivatives, for use as acaricidal/insecticidal/molluscicidal/nematicidal agents, or in controlling invertebrate pests, are described in WO2013/162715, WO2013/162716, WO2013/062981 and WO2012/061290.

The present invention is based on the finding that pyridino-pyrazole, and pyrimidino-pyrazole derivatives of formula (I) as defined herein, exhibit surprisingly good herbicidal activity.

Thus, in a first aspect of the invention there is provided the use of a compound of formula (I),

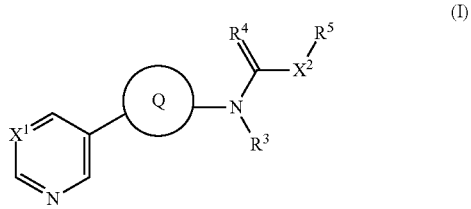

(I)

or a salt or N-oxide thereof, wherein Q is a ring system selected from

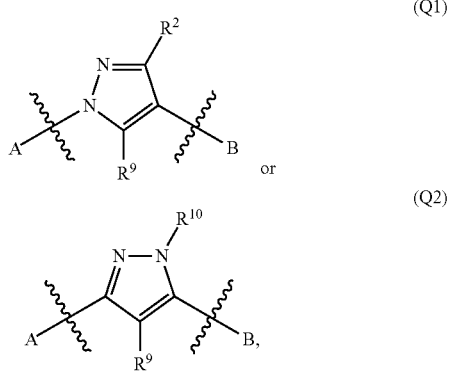

wherein A denotes the point of attachment to the heteroaryl ring, and B denotes the point of attachment to the nitrogen atom;

$X_1$ is N or $CR^1$;

$R^1$ is hydrogen, halogen, cyano, $C_1$-$C_6$ alkyl, $C_3$-$C_6$ cycloalkyl, $C_2$-$C_6$ alkenyl, $C_2$-$C_6$ alkynyl, $C_1$-$C_6$ alkoxy, $C(O)OR^6$ or $S(O)_n(C_1$-$C_6$ alkyl), formyl, hydroxyl, —$C(O)NR^6R^7$, $NR^6R^7$, benzyloxy, $C_1$-$C_6$ haloalkoxy, or $C_1$-$C_6$ haloalkyl;

$R^2$ is hydrogen, halogen, cyano, nitro, $C_1$-$C_6$ alkyl, $C_1$-$C_6$ haloalkyl, $C_2$-$C_6$ alkenyl, $C(O)OR^6$, or $S(O)_n(C_1$-$C_6$ alkyl), $C_1$-$C_6$ alkoxy, $C_1$-$C_6$ haloalkoxy;

n is 0, 1, or 2;

$R^3$ is hydrogen, cyano, $C_1$-$C_6$ alkyl, $C_2$-$C_6$ alkenyl, $C_2$-$C_6$ alkynyl, $C_2$-$C_6$ haloalkenyl, $C_1$-$C_6$ alkoxy, $C_1$-$C_6$ haloalkyl, $C_1$-$C_6$ haloalkoxy, $C_2$-$C_6$ alkenyloxy, $C_3$-$C_{10}$ cycloalkyl, $NR^6R^7$;

$R^4$ is O, S, or $N(C_1$-$C_6$ alkyl);

$X^2$ is O, S, or $NR^8$;

$R^5$ is hydrogen, $C_1$-$C_6$ alkyl, $C_2$-$C_6$ alkenyl, $C_2$-$C_6$ alkynyl, $C_3$-$C_{10}$ cycloalkyl, $C_3$-$C_{10}$ cycloalkenyl, $C_1$-$C_6$ haloalkyl, $C_2$-$C_6$ haloalkenyl, $C_1$-$C_6$ alkoxy, $C_1$-$C_6$ haloalkoxy, $C_2$-$C_6$ alkenyloxy, $C_2$-$C_6$ alkynyloxy, $C_3$-$C_{10}$ cycloalkyloxy, $C_3$-$C_{10}$ cycloalkenyloxy, $C_2$-$C_6$ haloalkenyloxy, $C_6$-$C_{10}$ aryl or $C_6$-$C_{10}$ aryl substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; $C_3$-$C_{10}$ heterocyclyl or $C_3$-$C_{10}$ heterocyclyl substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; or $NR^6R^7$;

or $R^3$ and $R^5$ together with $X^2$ and the atoms to which they are attached, form a saturated or partially unsaturated 5-9 membered ring system optionally comprising 1 to 3 heteroatoms independently selected from S, O and N and optionally substituted with 1 to 3 groups independently selected from halogen or $C_1$-$C_6$ alkyl;

or $R^3$ and $R^8$ together with the atoms to which they are attached form a saturated or partially unsaturated 5-9 membered ring system optionally comprising 1 to 3 heteroatoms independently selected from S, O and N and optionally substituted with 1 to 3 groups independently selected from halogen or $C_1$-$C_6$ alkyl;

$R^6$ and $R^7$ are each independently hydrogen, $C_1$-$C_6$ alkyl, $C_1$-$C_6$ haloalkyl, $C_2$-$C_6$ alkenyl, or $C_2$-$C_6$ alkynyl, or $R^6$ and $R^7$ together with the nitrogen atom to which they are attached form a saturated or partially unsaturated 3-6 membered ring optionally comprising 1 to 3 heteroatoms independently selected from S, O and N and optionally substituted with 1 to 3 groups independently selected from halogen or $C_1$-$C_6$ alkyl;

$R^8$ is hydrogen, cyano, $C_1$-$C_6$ alkyl, $C_1$-$C_6$ haloalkyl, $C_2$-$C_6$ alkenyl, or $C_2$-$C_6$ alkynyl; $C_1$-$C_6$ alkoxy, $C_1$-$C_6$ haloalkoxy, $C_2$-$C_6$ alkenyloxy, $C_2$-$C_6$ alkynyloxy, $C_3$-$C_{10}$ cycloalkyloxy, $C_3$-$C_{10}$ cycloalkenyloxy, $C_2$-$C_6$ haloalkenyloxy;

or $R^7$ and $R^8$ together with the carbon atoms to which they are attached form a saturated or partially unsaturated 3-9 membered ring optionally comprising 1 to 3 heteroatoms independently selected from S, O and N and optionally substituted with 1 to 3 groups independently selected from halogen or $C_1$-$C_6$ alkyl, $R^9$ is hydrogen, halogen, cyano, $C_1$-$C_6$ alkyl, $C_1$-$C_6$ haloalkyl, $C_2$-$C_6$ alkenyl, $C_2$-$C_6$ alkynyl, $C_1$-$C_6$ haloalkoxy, $C_1$-$C_6$ alkoxy, or $C_3$-$C_6$ cycloalkyl;

$R^{10}$ is hydrogen, $C_1$-$C_6$ alkyl, $C_1$-$C_6$ haloalkyl, $C_2$-$C_6$ alkenyl, $C_1$-$C_6$ alkylsulfinyl, $C_1$-$C_6$ alkylsulfonyl, $C_1$-$C_6$ alkylthio, —$C(O)OR^6$, $C_1$-$C_6$ alkoxy, $C_1$-$C_6$ haloalkoxy, $C_3$-$C_6$ cycloalkyl, or $C_2$-$C_6$ alkynyl, as a herbicide.

Compounds of formula (I) may exist as different geometric isomers, or in different tautomeric forms. This invention covers the use of all such isomers and tautomers, and mixtures thereof in all proportions, as well as isotopic forms such as deuterated compounds.

It may be the case that compounds of formula (I) contain one or more asymmetric centers and may thus give rise to optical isomers and diastereomers. While shown without respect to stereochemistry, the present invention includes the use of all such optical isomers and diastereomers as well as the racemic and resolved, enantiomerically pure R and S stereoisomers and other mixtures of the R and S stereoisomers and agrochemically acceptable salts thereof.

Each alkyl moiety either alone or as part of a larger group (such as alkoxy, alkylthio, alkoxycarbonyl, alkylcarbonyl, alkylaminocarbonyl, or dialkylaminocarbonyl, et al.) may be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups are generally $C_1$-$C_6$ alkyl groups (except where already defined more narrowly), but are preferably $C_1$-$C_4$ alkyl or $C_1$-$C_3$ alkyl groups, and, more preferably, are $C_1$-$C_2$ alkyl groups (such as methyl).

Alkenyl and alkynyl moieties can be in the form of straight or branched chains, and the alkenyl moieties, where appropriate, can be of either the (E)- or (Z)-configuration. Alkenyl and alkynyl moieties can contain one or more double and/or triple bonds in any combination, but preferably contain only one double bond (for alkenyl) or only one triple bond (for alkynyl).

The alkenyl or alkynyl moieties are typically $C_2$-$C_4$alkenyl or $C_2$-$C_4$alkynyl, more specifically ethenyl (vinyl), prop-2-enyl (allyl), ethynyl, prop-2-ynyl (propargyl), or prop-1-ynyl.

Preferably, the term cycloalkyl refers to cyclopropyl, cyclobutyl, cyclopentyl or cyclohexyl.

In the context of the present specification the term "aryl" preferably means phenyl. The term "heteroaryl" as used herein means an aromatic ring system containing at least one ring heteroatom and consisting of a single ring. Preferably, single rings will contain 1, 2 or 3 ring heteroatoms selected independently from nitrogen, oxygen and sulfur. Typically "heteroaryl" is furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, or 1,3,5-triazinyl.

Heterocyclyl groups and heterocyclic rings (either alone or as part of a larger group, such as heterocyclyl-alkyl-) are ring systems containing at least one heteroatom and can be in mono- or bi-cyclic form. Preferably, heterocyclyl groups will contain up to two heteroatoms which will preferably be chosen from nitrogen, oxygen and sulfur.

Examples of heterocyclic groups include oxetanyl, thietanyl, azetidinyl and 7-oxabicyclo[2.2.1]hept-2-yl. Heterocyclyl groups containing a single oxygen atom as heteroatom are most preferred. The heterocyclyl groups are preferably 3- to 8-membered, more preferably 3- to 6-membered rings.

Halogen (or halo) encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl, 2,2,2-trichloroethyl, heptafluoro-n-propyl and perfluoro-n-hexyl.

Alkoxy groups preferably have a chain length of from 1 to 6 carbon atoms. Alkoxy is, for example, methoxy, ethoxy, n-propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents may be present on the same carbon atom.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$ alkyl-S— (alkylthio) is, for example, methylthio, ethylthio, n-propylthio, isopropylthio, n-butylthio, isobutylthio, sec-butylthio or tert-butylthio, preferably methylthio or ethylthio.

$C_1$-$C_6$ alkyl-S(O)— (alkylsulfinyl) is, for example, methylsulfinyl, ethylsulfinyl, n-propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$ alkyl-S(O)$_2$— (alkylsulfonyl) is, for example, methylsulfonyl, ethylsulfonyl, n-propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Compounds of formula (I) may form, and/or be used as, agronomically acceptable salts with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

Compounds of formula (I) may also form (and/or be used as) agronomically acceptable salts with various organic and/or inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids, when the compound of formula (I) contains a basic moiety.

Compounds of formula (I) may also be in the form of/used as hydrates which may be formed during the salt formation.

Preferred values of $X_1$, $X^2$, $R^1$, $R^2$, $R^3$, $R^4$, $R^5$, $R^6$, $R^7$, $R^8$, $R^9$, $R^{10}$ and n are as set out below, and a compound of formula (I) according to the invention may comprise any combination of said values. The skilled person will appreciate that values for any specified set of embodiments may be combined with values for any other set of embodiments where such combinations are not mutually exclusive.

Preferably $R^1$ is hydrogen, halogen, formyl, cyano, $C_1$-$C_6$ alkoxy, $C_1$-$C_6$ alkylsulfonyl, $C_1$-$C_6$ alkylthio, $C_1$-$C_6$ haloalkoxy, —C(O)NR$^6$R$^7$, NR$^6$R$^7$, or $C_1$-$C_6$ haloalkyl. More preferably $R^1$ is hydrogen, fluorine, chlorine, cyano, trifluoromethyl, methoxy, difluoromethoxy, formyl, methanesulfonyl, carboxamide, methanethiol or amino.

Preferably $R^2$ is halogen, cyano, nitro, $C_1$-$C_6$ alkyl, $C_1$-$C_6$ haloalkyl, $C_2$-$C_6$ alkenyl, $C_1$-$C_6$ alkylsulfinyl, $C_1$-$C_6$ alkylsulfonyl, $C_1$-$C_6$ alkylthio, —C(O)OR$^6$, $C_1$-$C_6$ alkoxy, $C_1$-$C_6$ haloalkoxy, $C_3$-$C_6$ cycloalkyl, or $C_2$-$C_6$ alkynyl. More preferably $R^2$ is halogen, cyano, $C_1$-$C_6$ alkyl, $C_1$-$C_6$ haloalkyl, $C_2$-$C_6$ alkenyl, $C_1$-$C_6$ alkoxy, $C_1$-$C_6$ haloalkoxy, $C_3$-$C_6$ cycloalkyl, —C(=O)OR$^6$, or $C_2$-$C_6$ alkynyl. Even more preferably $R^2$ is methyl, trifluoromethyl, chloro, bromo, iodo, fluoro, vinyl, ethynyl, methoxycarbonyl, —$CO_2H$, or cyclopropyl; As stated above, $R^3$ is $C_1$-$C_6$ alkyl, $C_2$-$C_6$ alkenyl, $C_2$-$C_6$ alkynyl, $C_2$-$C_6$ haloalkenyl, $C_1$-$C_6$ alkoxy, $C_1$-$C_6$ haloalkyl, $C_1$-$C_6$ haloalkoxy, $C_2$-$C_6$ alkenyloxy, $C_3$-$C_{10}$ cycloalkyl, or $NR^6R^7$. Preferably $R^3$ is hydrogen, or $C_1$-$C_3$ alkyl. More preferably, $R^3$ is hydrogen or methyl.

Preferably $R^4$ is O.

Preferably $X^2$ is O, or $NR^8$.

Preferably $R^5$ is $C_1$-$C_6$ alkyl, $C_2$-$C_6$ alkenyl, $C_2$-$C_6$ alkynyl, $C_3$-$C_{10}$ cycloalkyl, $C_1$-$C_6$ haloalkyl, $C_2$-$C_6$ haloalkenyl, $C_1$-$C_6$ alkoxy, $C_1$-$C_6$ haloalkoxy, $C_2$-$C_6$ alkenyloxy, $C_2$-$C_6$ alkynyloxy, $C_3$-$C_{10}$ cycloalkyloxy, $C_3$-$C_{10}$ cycloalkenyloxy, $C_2$-$C_6$ haloalkenyloxy, $C_6$-$C_{20}$ aryl, $C_3$-$C_{20}$ heterocyclyl, or $NR^6R^7$. More preferably $R^5$ is methyl, ethyl, iso-propyl, tert-butyl, or tert-butoxy.

Preferably $R^8$ is hydrogen, cyano, $C_1$-$C_6$ alkyl, $C_1$-$C_6$ haloalkyl, $C_2$-$C_6$ alkenyl, or $C_2$-$C_6$ alkynyl.

Preferably $R^9$ is hydrogen, chloro, fluoro, bromo, methyl or trifluoromethyl. More preferably $R^9$ is hydrogen, chloro, fluoro or bromo. Even more preferably $R^9$ is hydrogen or chloro.

Preferably $R^{10}$ is, $C_1$-$C_6$ alkyl, $C_1$-$C_6$ haloalkyl, $C_2$-$C_6$ alkenyl, $C_1$-$C_6$ alkylsulfinyl, $C_1$-$C_6$ alkylsulfonyl, $C_1$-$C_6$ alkylthio, —$C(O)OR^6$, $C_1$-$C_6$ alkoxy, $C_1$-$C_6$ haloalkoxy, $C_3$-$C_6$ cycloalkyl, or $C_2$-$C_6$ alkynyl. More preferably $R^{10}$ is $C_1$-$C_6$ alkyl, $C_1$-$C_6$ haloalkyl, $C_2$-$C_6$ alkenyl, $C_1$-$C_6$ alkoxy, $C_1$-$C_6$ haloalkoxy, $C_3$-$C_6$ cycloalkyl, —$C(O)OR^6$ or $C_2$-$C_6$ alkynyl. Even more preferably $R^{10}$ is methyl, trifluoromethyl or difluoromethyl.

In embodiments where $R^3$ and $R^5$, together with $X^2$ and the atoms to which they are attached, form a saturated or partially unsaturated 5-9 membered ring system optionally comprising 1 to 3 heteroatoms independently selected from S, O and N and optionally substituted with 1 to 3 groups independently selected from halogen or $C_1$-$C_6$ alkyl, it is preferred that the following groups T (i.e. $T_1$, or $T_2$) are formed:

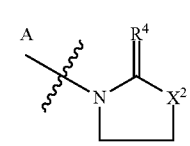

$T_1$

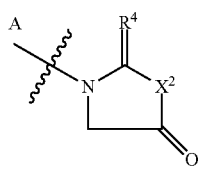

$T_2$ wherein $X^2$ and $R^4$ are as defined herein, and A denotes the point of attachment to the pyridino/pyrimidino-pyrazole moiety. Preferably in groups $T_1$ and $T_2$, $R^4$ is O and $X^2$ is O or $NR^8$. Even more preferably, $R^4$ is O and $X_2$ is O or $NR^8$ and $R^8$ is methyl.

Table 1 below provides specific examples of herbicidal compounds of formula (I) for use according to the invention.

TABLE 1

Compounds of formula (I)

| Cmpd | Structure |
|------|-----------|
| A1 | 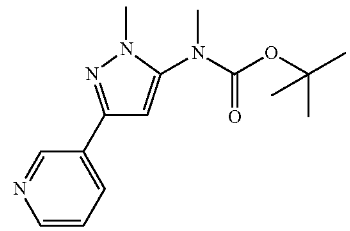 [SMILES: CN(C(=O)OC(C)(C)C)c1cc(-c2cccnc2)nn1C] |
| A2 | 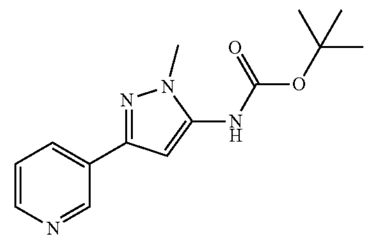 [SMILES: Cn1nc(-c2cccnc2)cc1NC(=O)OC(C)(C)C] |
| A3 | 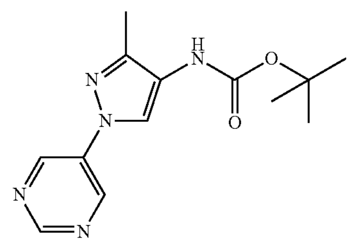 [SMILES: Cc1nn(-c2cncnc2)cc1NC(=O)OC(C)(C)C] |
| A4 | 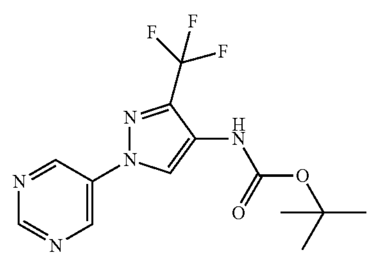 [SMILES: CC(C)(C)OC(=O)Nc1cn(-c2cncnc2)nc1C(F)(F)F] |
| A5 | 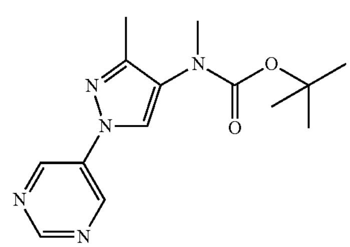 [SMILES: Cc1nn(-c2cncnc2)cc1N(C)C(=O)OC(C)(C)C] |
| A6 | 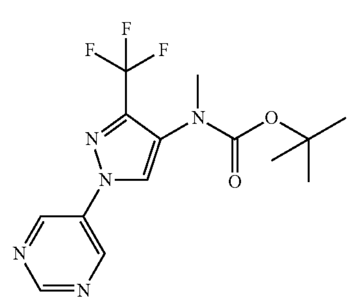 [SMILES: CN(C(=O)OC(C)(C)C)c1cn(-c2cncnc2)nc1C(F)(F)F] |

TABLE 1-continued
Compounds of formula (I)
| Cmpd | Structure |
|---|---|
| A7 | 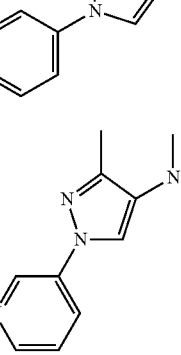 |
| A8 | 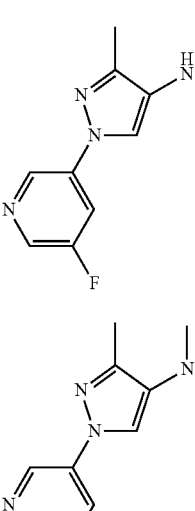 |
| A9 | 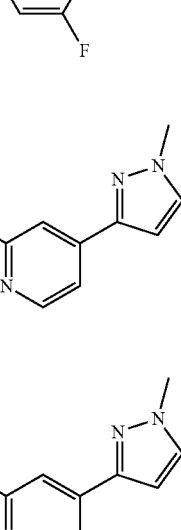 |
| A10 | 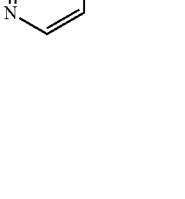 |
| A11 | 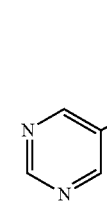 |
| A12 | 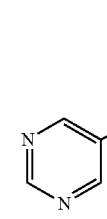 |
| A13 | 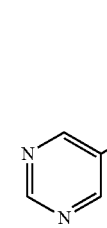 |
| A14 | 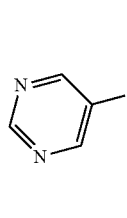 |
| A15 | 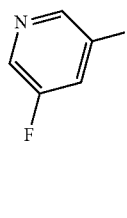 |
| A16 | 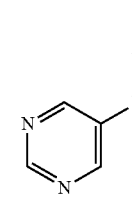 |
| A17 | |
| A18 | |

TABLE 1-continued

Compounds of formula (I)

| Cmpd | Structure |
|---|---|
| A19 | 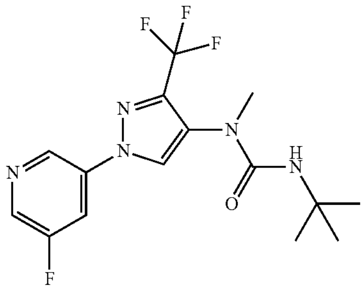 [SMILES: CN(C(=O)NC(C)(C)C)c1cn(-c2cncc(F)c2)nc1C(F)(F)F] |
| A20 | 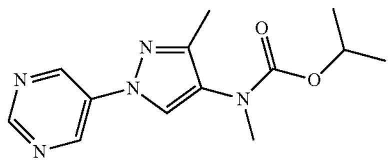 [SMILES: Cc1nn(-c2cncnc2)cc1N(C)C(=O)OC(C)C] |
| A21 | 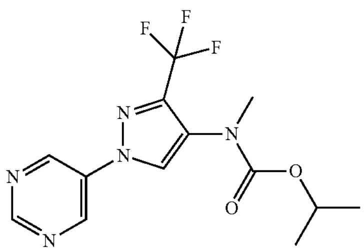 [SMILES: CC(C)OC(=O)N(C)c1cn(-c2cncnc2)nc1C(F)(F)F] |
| A22 | 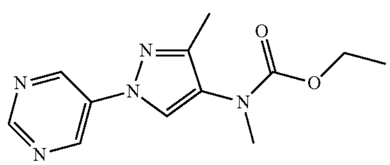 [SMILES: CCOC(=O)N(C)c1cn(-c2cncnc2)nc1C] |
| A23 | 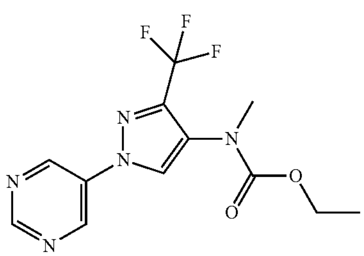 [SMILES: CCOC(=O)N(C)c1cn(-c2cncnc2)nc1C(F)(F)F] |
| A24 | 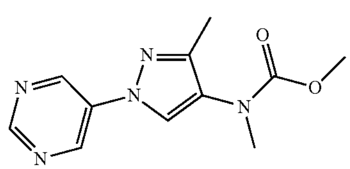 [SMILES: COC(=O)N(C)c1cn(-c2cncnc2)nc1C] |
| A25 | 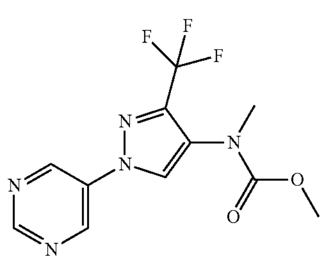 [SMILES: COC(=O)N(C)c1cn(-c2cncnc2)nc1C(F)(F)F] |
| A26 | |
| A27 | |
| A30 | |
| A31 | |
| A32 | |
| A33 | |

TABLE 1-continued

Compounds of formula (I)

| Cmpd | Structure |
|---|---|
| A34 | 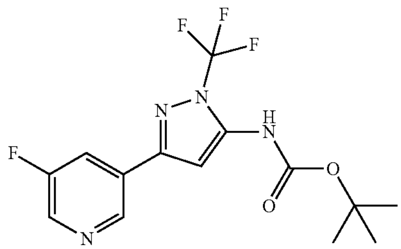 [SMILES: CC(C)(C)OC(=O)Nc1cc(-c2cncc(F)c2)nn1C(F)(F)F] |
| A35 | 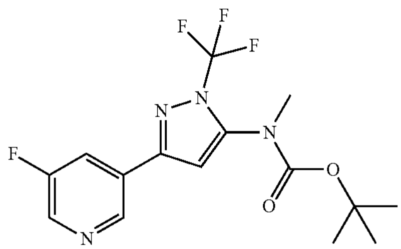 [SMILES: CN(C(=O)OC(C)(C)C)c1cc(-c2cncc(F)c2)nn1C(F)(F)F] |
| A36 | 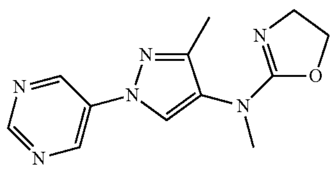 [SMILES: Cc1nn(-c2cncnc2)cc1N(C)C1=NCCO1] |
| A37 | 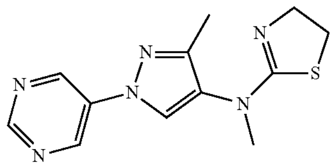 [SMILES: Cc1nn(-c2cncnc2)cc1N(C)C1=NCCS1] |
| A38 | 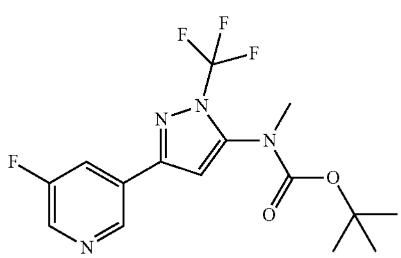 [SMILES: CN(C(=O)OC(C)(C)C)c1cc(-c2cncc(F)c2)nn1C(F)(F)F] |
| A39 | 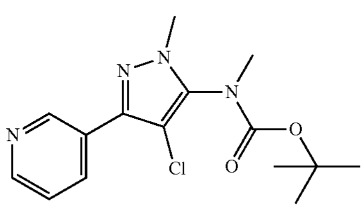 [SMILES: CN(C(=O)OC(C)(C)C)c1c(Cl)c(-c2cccnc2)nn1C] |
| A40 | 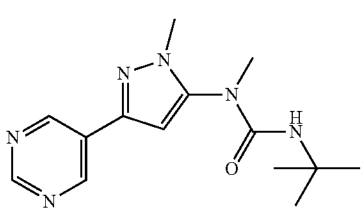 [SMILES: CN(C(=O)NC(C)(C)C)c1cc(-c2cncnc2)nn1C] |
| A41 | |
| A42 | |
| A43 | |
| A44 | |
| A45 | |
| A46 | |

TABLE 1-continued

Compounds of formula (I)

| Cmpd | Structure |
|------|-----------|
| A47 | 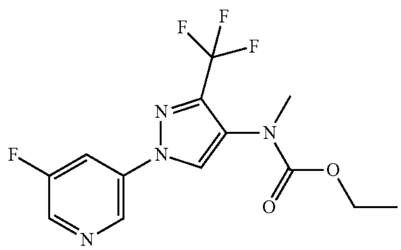 [SMILES: CCOC(=O)N(C)c1cn(-c2cncc(F)c2)nc1C(F)(F)F] |
| A48 | 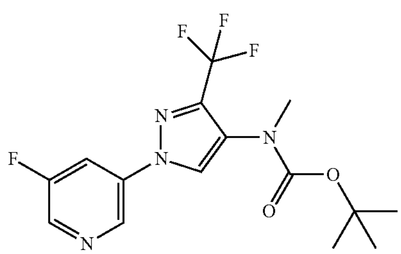 [SMILES: CN(C(=O)OC(C)(C)C)c1cn(-c2cncc(F)c2)nc1C(F)(F)F] |
| A49 | 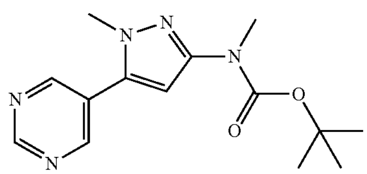 [SMILES: CN(C(=O)OC(C)(C)C)c1cc(-c2cncnc2)n(C)n1] |
| A51 | 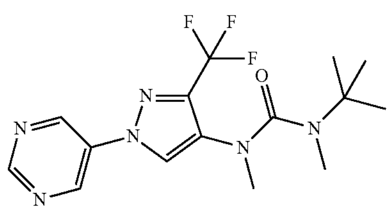 [SMILES: CN(C(=O)N(C)C(C)(C)C)c1cn(-c2cncnc2)nc1C(F)(F)F] |
| A52 | 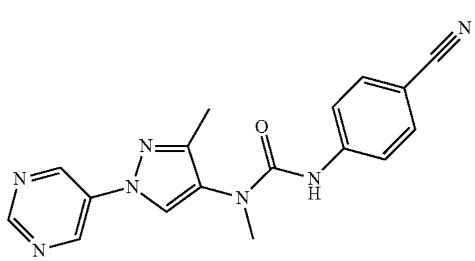 [SMILES: Cc1nn(-c2cncnc2)cc1N(C)C(=O)Nc1ccc(C#N)cc1] |
| A53 | 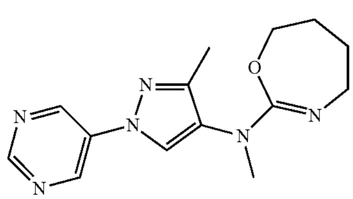 [SMILES: Cc1nn(-c2cncnc2)cc1N(C)C1=NCCCCO1] |
| A54 | |
| A55 | |
| A56 | |
| A57 | |
| A58 | |
| A59 | |

TABLE 1-continued

Compounds of formula (I)

| Cmpd | Structure |
|---|---|
| A60 | (tert-butyl N-methyl-N-[3-chloro-1-(pyridin-3-yl)pyrazol-4-yl]carbamate structure) |

Compounds of Formula (I) may be prepared according to the following schemes, in which the substituents $X_1$, $X^2$, $R^1$, $R^2$, $R^3$, $R^4$, $R^5$, $R^6$, $R^7$, $R^8$, $R^9$, $R^{10}$ and n have (unless otherwise stated explicitly) the definitions described hereinbefore, using techniques known to the person skilled in the art of organic chemistry. General methods for the production of compounds of Formula (I) are described below. Unless otherwise stated in the text the synthetic procedures are derived from WO2013/162715, WO2013/162716, WO2013/062981 and WO2012/061290. The starting materials used for the preparation of the compounds of the invention may be purchased from the usual commercial suppliers or may be prepared by known methods. The starting materials as well as the intermediates may be purified before use by state of the art methodologies such as chromatography, crystallization, distillation and filtration.

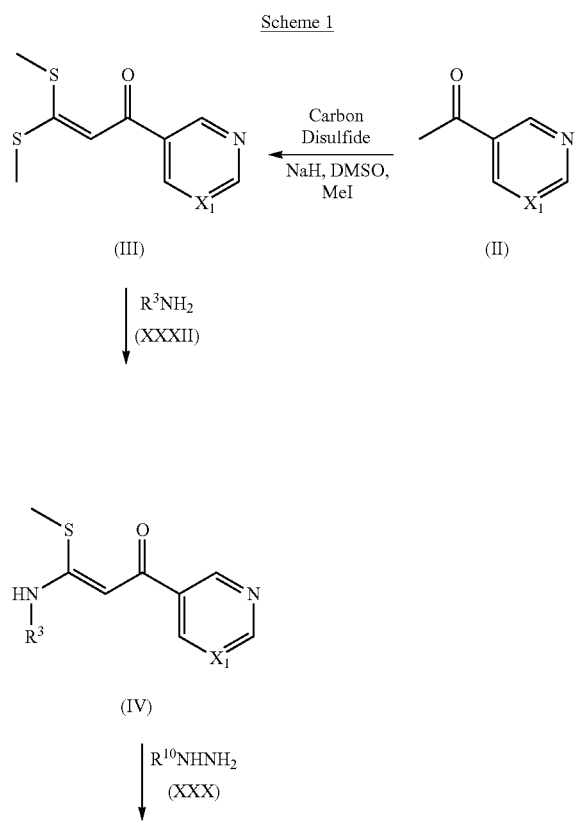

Scheme 1

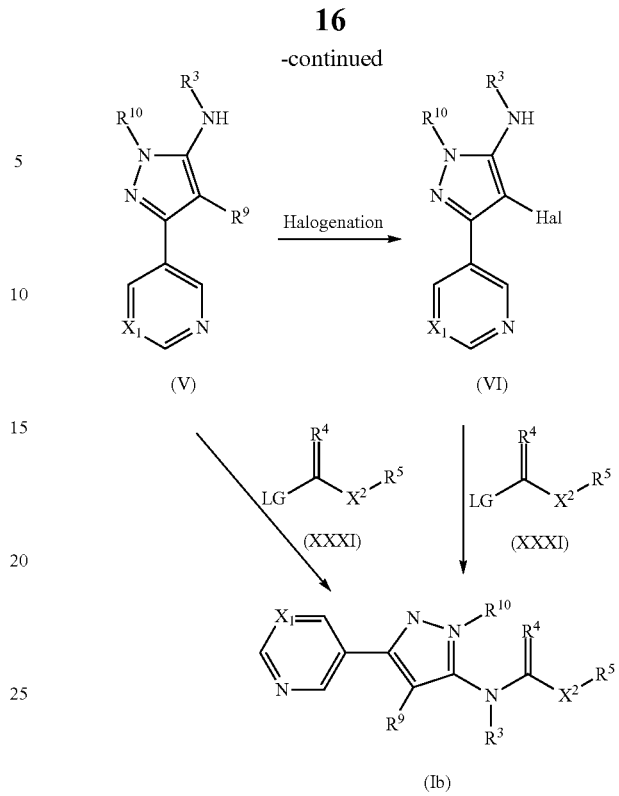

As illustrated in Scheme 1 above, treatment of an appropriately substituted heterocyclic methyl ketone of Formula (II) with carbon disulphide and iodomethane in the presence of a suitable base (such as sodium hydride) and a suitable solvent (such as DMSO) leads to compounds of Formula (III). Compounds of Formula (III) can be treated with a suitable amine of Formula (XXXII) in the presence of a base (such as triethylamine) in a solvent (such as ethanol) to afford compounds of Formula (IV) and/or their stereoisomers.

Compounds of Formula (IV) can be further converted to an aminopyrazole of Formula (V) via treatment with an appropriately substituted hydrazine of Formula (XXX) in a polar protic solvent (such as ethanol) as described in WO2013/162716. The resulting amino pyrazole of Formula (V) can be further elaborated by reaction with an appropriate reagent of Formula (XXXI), where LG is a suitable leaving group (for example, the reagent (XXXI) is di-tert-butyl dicarbonate) in the presence of a suitable base (such as pyridine) in an aprotic solvent (such as dichloromethane) or under conditions where an excess of a base (such as pyridine) is used as solvent to afford compounds of Formula (Ib).

Alternatively when $R^9$=H the compounds of Formula (V) may be halogenated by a suitable reagent (such as N-chlorosuccinimide) in a suitable solvent (such as acetonitrile) to give compounds of Formula (VI) which in turn can be further elaborated by reaction with an appropriate reagent of Formula (XXXI) (for example di-tert-butyl dicarbonate) in the presence of a suitable base (such as pyridine) in an aprotic solvent (such as dichloromethane) or under conditions where an excess of a base (such as pyridine) is used as solvent, to afford (Ib).

As illustrated in Scheme 2 below, compounds of Formula (Ib) can be prepared via a sequence starting from β-diketo esters (such as ethyl 2,4-dioxo-4-(3-pyridyl)butanoate) which can be prepared by condensation of an appropriately substituted heteroaryl ketone of Formula (II) with a diester of oxalic acid (such as diethyl oxalate) in the presence of a suitable base (such as sodium hydride) in a suitable solvent (such as THF).

β-Diketo esters of Formula (VII) can be reacted with a suitably substituted hydrazine of Formula (XXX) in a polar protic solvent (for example ethanol) to give pyrazine esters under mild conditions (using, for example sodium hydride in a polar aprotic solvent like N,N-dimethylformamide) with a suitable alkylating agent of Formula (XXXIV), where LG is a suitable leaving group (an example of such an alkylating reagent is methyl iodide) to give compounds of Formula (Ib).

Scheme 2

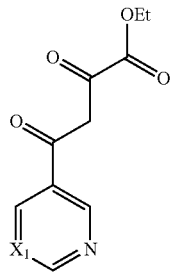
(VII)

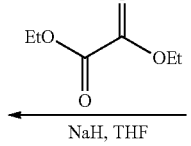
NaH, THF

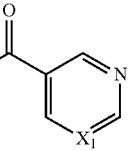
(II)

$R^{10}NHNH_2$
(XXX)

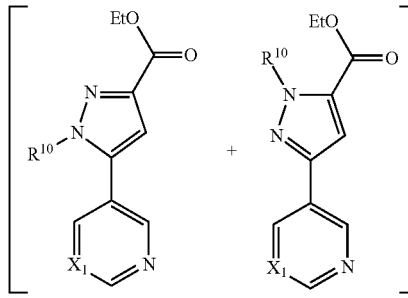
(VIII)

Hydrolysis

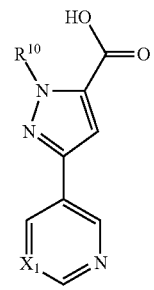
(IX)

1. Curtius rearrangement
$R^5X^2H$
(XXXIII)

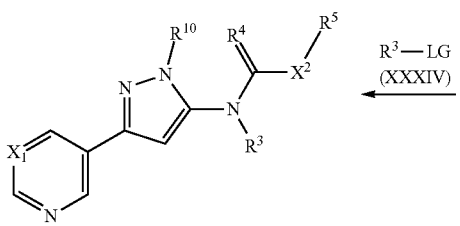
(Ib)

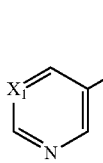 $R^3$—LG
(XXXIV)

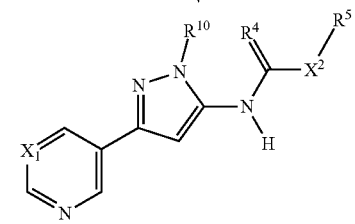
(Ic)

of Formula (VIII). Basic saponification under typical conditions (for example sodium hydroxide, water and 1,4-dioxane), followed by separation where required, gives acids of Formula (IX) which can be reacted to form an acyl azide with suitable reagents such as diphenylphosphoryl azide (DPPA), which undergoes a Curtius reaction in-situ to generate an isocyanate which is then quenched by a suitable alcohol of Formula (XXXIII) ($X^2$=O) to give carbamates of Formula (Ic). These carbamates can then be further alkylated As illustrated in Scheme 3 above, another approach to the preparation of compounds of Formula (Ib) is via compounds of Formula (X) (which can be prepared by various known methods, including, but not limited to, those described by Ridge et al., in *J. Med. Chem.* 1979, 22, 1385-1389). Compounds of Formula (X) can be condensed with an appropriate hydrazine of Formula (XXX) to give regioisomeric aminopyrazoles of Formula (XI).

The resulting aminopyrazoles of Formula (XI) can be further elaborated by reaction with an appropriate reagent of Formula (XXXI) (such as di-tert-butyl dicarbonate) in the presence of a suitable base (such as pyridine) in an aprotic solvent (such as dichloromethane) or under conditions, where an excess of a base (such as pyridine) is used as solvent, to afford compounds of Formula (Ic) (after separation of the mixture of products formed) i.e. examples of the compounds of the invention in which $R^3$=H. Alkylation with a suitable electrophile of Formula (XXXIV) (such as methyl iodide) following deprotonation with a suitable base (such as sodium hydride) in a typical polar aprotic solvent (such as N,N-dimethylformamide) gives rise to compounds of Formula (Ib).

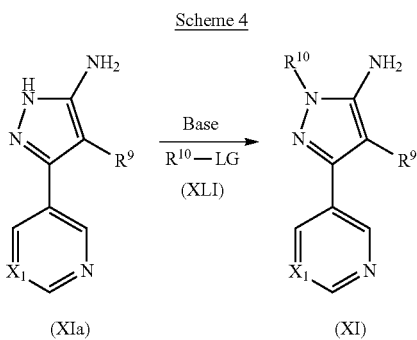

Scheme 4

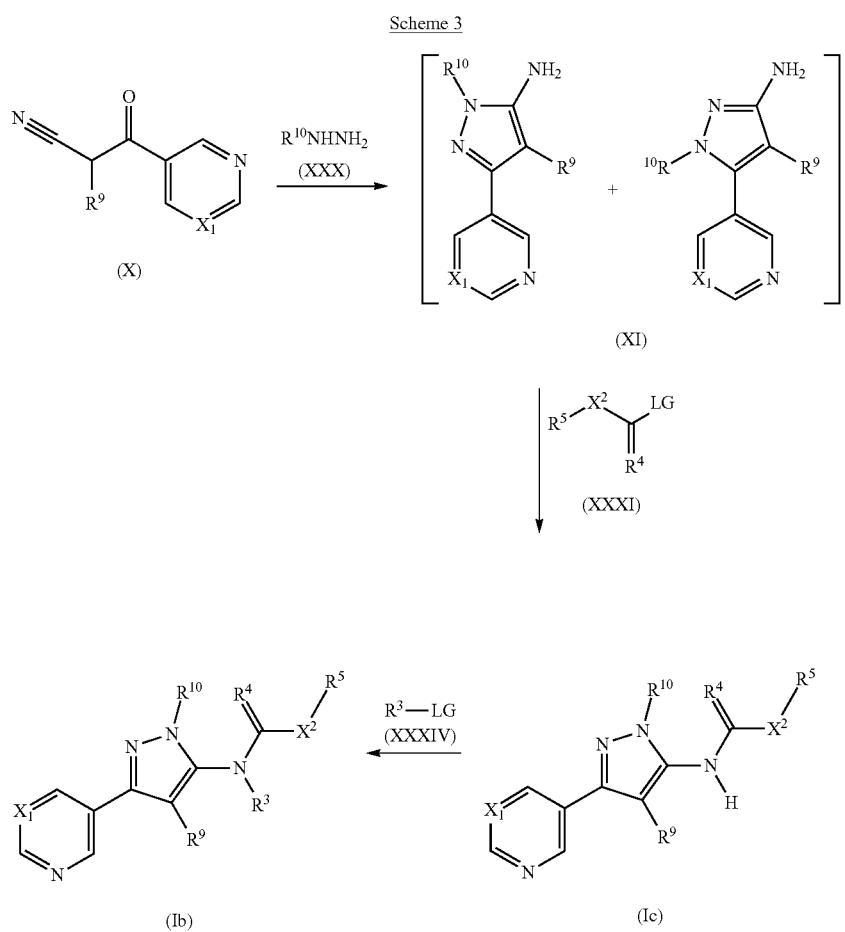

As illustrated in scheme 4 aminopyrazoles of Formula (XI) where $R^{10}$≠H can alternatively be prepared from aminopyrazoles of Formula (XIa) (compounds of Formula XI where $R^{10}$=H) via alkylation with a compound of Formula (XLI) (where LG is a suitable leaving group, such as Cl, Br, I or OTs) in the presence of a suitable base and in a suitable solvent. Suitable solvent/base combinations include $Cs_2CO_3$/DMF (see for example M. K. Ameriks et al Bioorg. Med. Chem, Lett. (2009), 613) and KOH/acetone (see for example G. Guillaumet et al Bioorg. Med. Chem. Lett. (2006), 1078).

As illustrated in Scheme 5, the nitro functionality of compounds of Formula (XII) can be reduced to an amine under hydrogenation conditions using hydrogen, a suitable catalyst (such as 5% Pd on alumina) and a solution of acid (for example 50% HBr) in a polar protic solvent (such as ethanol) to give compounds of Formula (XIII) (which can be isolated as salts e.g. as the HBr salts), as taught in WO2013/062981.

Compounds of Formula (XIII) can be converted to compounds of Formula (XIIV) using a suitable reagent of Formula (XXXI) (such as di-tert-butyl dicarbonate) in the presence of a mixture of solvents (such as water/THF) and a suitable base (such as sodium bicarbonate).

Compounds of Formula (XIIV) can be further converted to compounds of Formula (Id) by reaction with compounds of Formula (XV) in the presence of a catalytic amount of copper(II) chloride with a ligand (such as N,N'-dimethylethane-1,2-diamine) in a polar aprotic solvent (such as acetonitrile) with a suitable base (such as potassium phosphate) to afford compounds of Formula (Id), which are compounds of the invention, wherein $R^3$=H as taught in WO2013/062981. Further alkylation with a suitable alkylating agent of Formula (XXXIV) (for example methyl iodide) with a suitable base (such as sodium hydride) in a polar aprotic solvent (such as N,N-dimethylformamide) gives rise to compounds of Formula (Ia).

As illustrated in Scheme 6, when $R^4$=O, $X^2$=O and $R^5$=t-Bu, the resulting N-Boc group may be removed under mild acidic conditions, such as with HCl in ether, to afford an amine salt, such as the HCl salt. Acidic cleavage of compounds of Formula (I) (for example with HCl in a solvent such as tetrahydrofuran) gives compounds of Formula (XVI) as their salts, e.g. their HCl salts. Compounds of Formula (XVI) may then be further converted to compounds such as those of Formula (If) by reaction with a suitable chloroformate of Formula (XXXV) (such as ethyl chloroformate) in the presence of a base such as pyridine.

Scheme 5

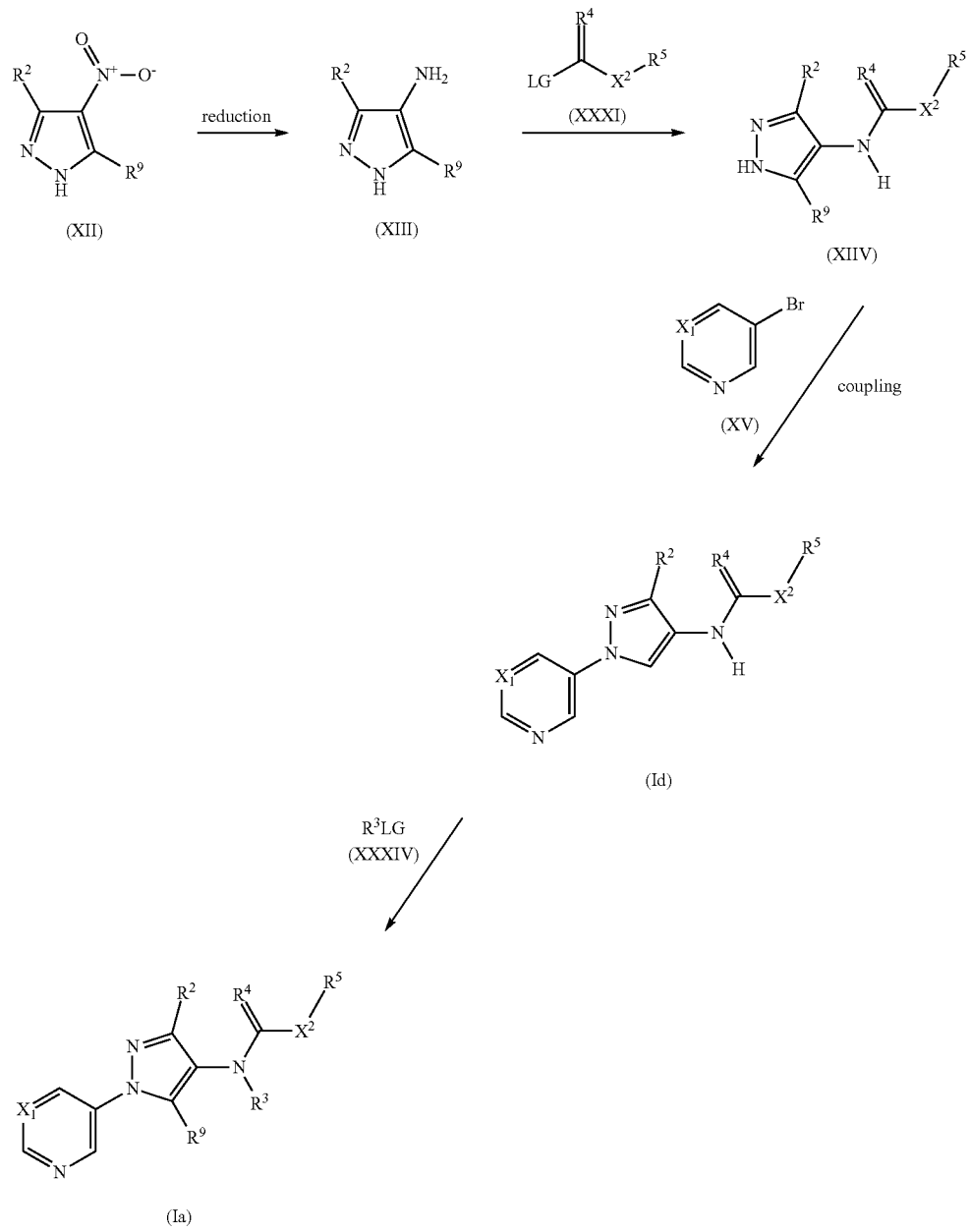

Scheme 6

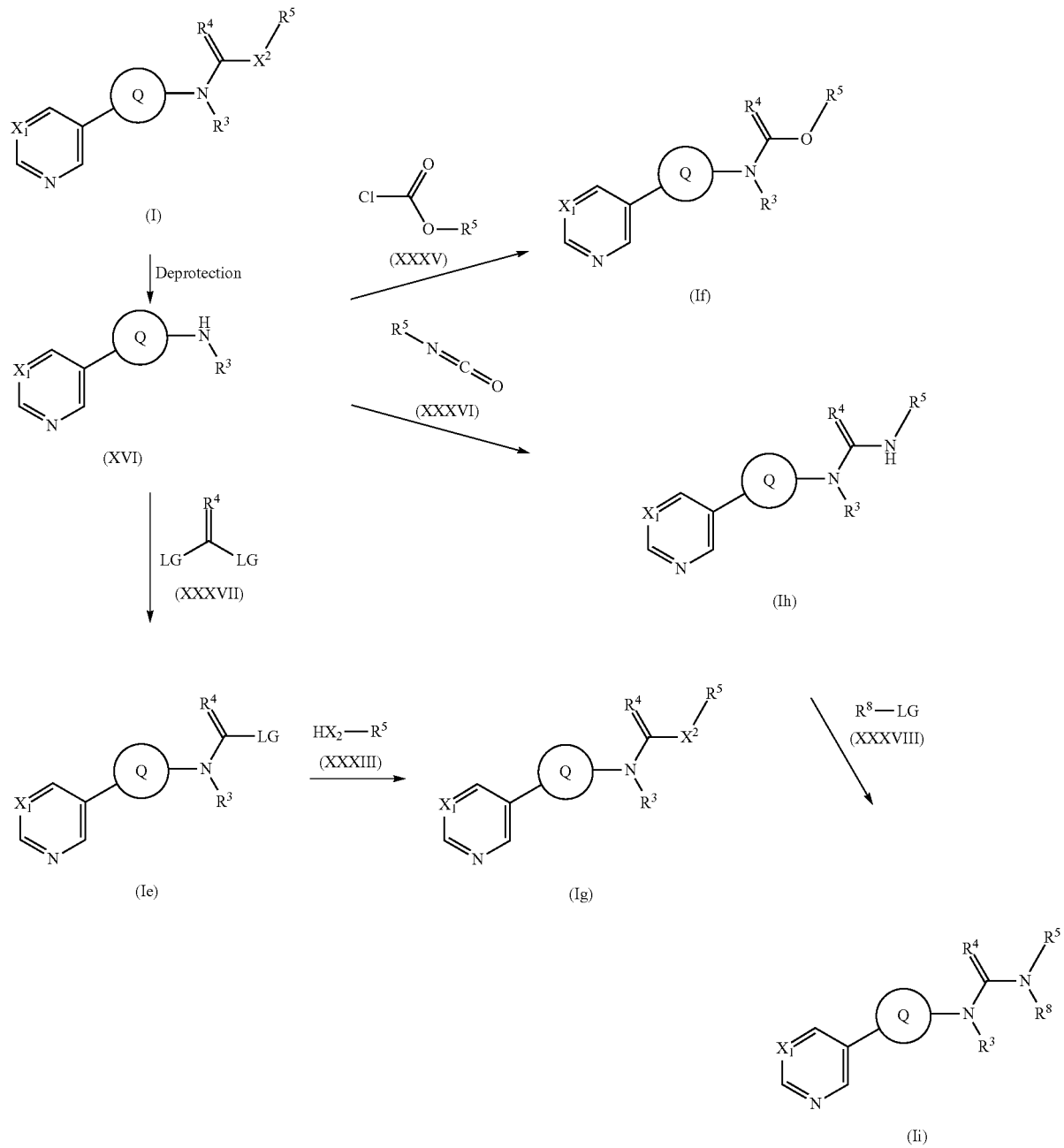

Alternatively, compounds of Formula (XVI) may then be further converted by reaction with phosgene or a suitable phosgene equivalent of Formula (XXXVII) (such as CDI or 4-nitrophenyl chloroformate) to give compounds of Formula (Ie). Further reaction with an alcohol, amine or thiol of Formula (XXXIII) then affords compounds of Formula (Ig).

As a further alternative, compounds of Formula (XVI) may be converted to compounds such as those of Formula (Ih) by reaction with a suitable isocyanate of Formula (XXXVI) (such as t-butyl-isonitrile). Where $X^2$=N, compounds of Formula (Ih) may be further alkylated with a suitable electrophile of Formula (XXXVIII) (for example methyl iodide) in the presence of a base (for example potassium carbonate) to give compounds of Formula (Ii).

Scheme 7

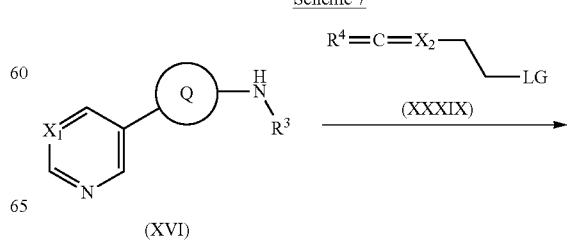

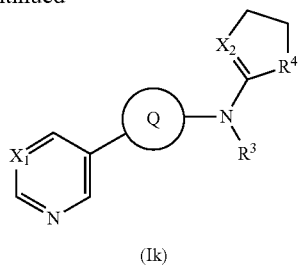

(Ik)

As illustrated in Scheme 7, compounds of Formula (XVI) can be converted to compounds of Formula (Ik) by treatment with a bifunctional reagent of Formula (XXXIX) (such as 1-chloro-2-isothiocyanoethane or 1-bromo-4-isocyanatobutane) in a solvent such as (1,4-dioxane) as taught in WO2013/186089.

formulated into herbicidal compositions using formulation adjuvants, such as carriers, solvents and surface-active agents (SFAs).

Thus, the present invention further provides a herbicidal composition comprising a herbicidal compound as described herein and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

Such herbicidal compositions generally comprise from 0.1 to 99% by weight, especially from 0.1 to 95% by weight of compounds of Formula (I) and from 1 to 99.9% by weight of a formulation adjuvant, which preferably includes from 0 to 25% by weight of a surface-active substance.

The compositions can be chosen from a number of formulation types, many of which are known from the Scheme 8

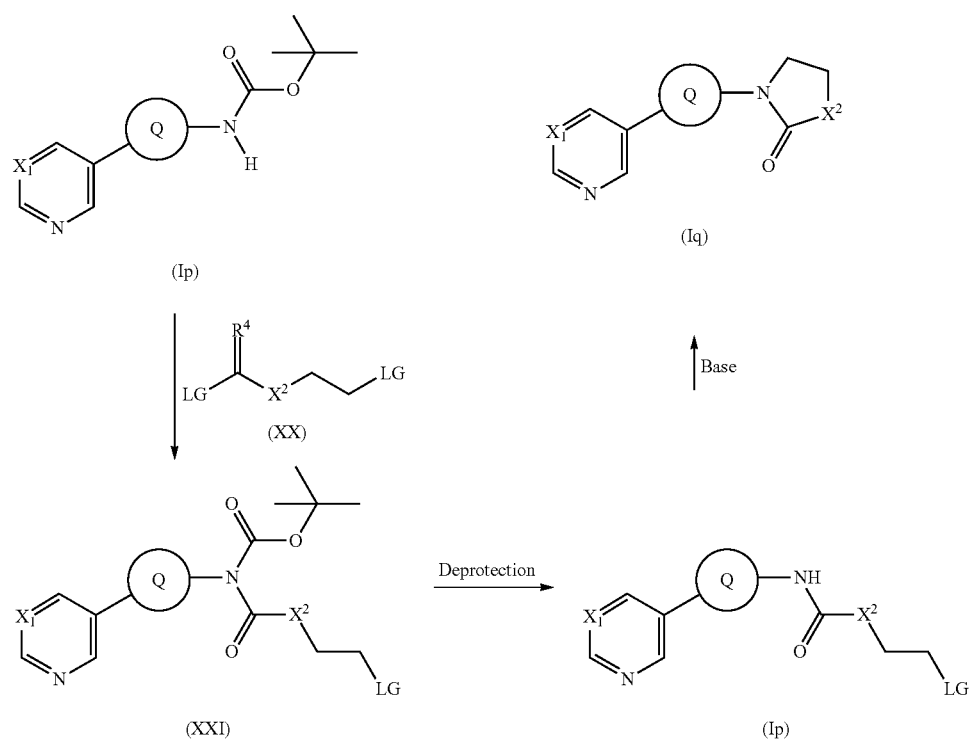

As illustrated in Scheme 8, acylation of a compound of Formula (Ip) with a bifunctional reagent of Formula (XX) (such as chloroethyl chloroformate) with a base (such as sodium hydride) in an ethereal solvent (such as 1,4-dioxane) affords compounds of Formula (XXI). The N-Boc group can be cleaved under mild conditions with acidic reagents (such as TFA) in a solvent (such as dichloromethane), to give compounds of Formula (Ip).

Compounds of Formula (Ip) can be further functionalised by cyclisation via deprotonation with a suitable base (such as sodium hydride) in a polar aprotic solvent (such as N,N-dimethylformamide) to give compounds of Formula (Iq).

The compounds of Formula (I) as described herein may be used as herbicides by themselves, but they are generally Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

Herbicidal compositions as described herein may further comprise at least one additional pesticide. For example, the compounds of formula (I) can also be used in combination with other herbicides or plant growth regulators. In a preferred embodiment the additional pesticide is a herbicide and/or herbicide safener. Examples of such mixtures are, in which 'I' represents a compound of Formula (I), I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6). The compounds of formula (I) and/or compositions of the present invention may also be combined with herbicidal compounds disclosed in WO06/024820 and/or WO07/096576.

The mixing partners of the compound of Formula (I) may also be in the form of esters or salts, as mentioned e.g. in The Pesticide Manual, Sixteenth Edition, British Crop Protection Council, 2012.

The compound of Formula (I) can also be used in mixtures with other agrochemicals such as fungicides, nematicides or insecticides, examples of which are given in The Pesticide Manual (supra).

The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula (I) as described herein can also be used in combination with one or more safeners. Likewise, mixtures of a compound of Formula (I) as described herein with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxybenzoylsulfamoyl)-benzamide (CAS RN 221668-34-4). Other possibilities include safener compounds disclosed in, for example, EP0365484 e.g N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methyl-aminocarbonyl) amino]benzenesulfonamide.

The safeners of the compound of Formula (I) may also be in the form of esters or salts, as mentioned e.g. in The Pesticide Manual (supra). The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula (I) to safener is from 100:1 to 1:10, especially from 20:1 to 1:1.

The mixtures can advantageously be used in the above-mentioned formulations (in which case "active ingredient" relates to the respective mixture of compound of Formula (I) with the safener).

As described above, compounds of formula (I) and/or compositions comprising such compounds may be used in methods of controlling unwanted plant growth, and in particular in controlling unwanted plant growth in crops of useful plants. Thus, the present invention further provides a method of selectively controlling weeds at a locus comprising crop plants and weeds, wherein the method comprises application to the locus, of a weed-controlling amount of a compound of formula (I), or a composition as described herein. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula (I) may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®. In a particularly preferred aspect, the crop plant has been engineered to overexpress homogentisate solanesyltransferase as taught in, for example, WO2010/029311.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod and ornamental plants such as flowers or bushes.

The compositions can be used to control unwanted plants (collectively, 'weeds').

The weeds to be controlled include both monocotyledonous (e.g. grassy) species, for example: *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*; and dicotyledonous species, for example: *Abutilon, Amaranthus, Ambrosia, Chenopodium, Chrysanthemum, Conyza, Galium, Ipomoea, Kochia, Nasturtium, Polygonum, Sida, Sinapis, Solanum, Stellaria, Veronica, Viola* and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

Preferably the weeds to be controlled and/or growth-inhibited, include monocotyledonous weeds, more preferably grassy monocotyledonous weeds, in particular those from the following genus: *Agrostis, Alopecurus, Apera, Avena, Brachiaria, Bromus, Cenchrus, Cyperus* (a genus of sedges), *Digitaria, Echinochloa, Eleusine, Eriochloa, Fimbristylis* (a genus of sedges), *Juncus* (a genus of rushes), *Leptochloa, Lolium, Monochoria, Ottochloa, Panicum, Pennisetum, Phalaris, Poa, Rottboellia, Sagittaria, Scirpus* (a genus of sedges), *Setaria* and/or *Sorghum*, and/or volunteer corn (volunteer maize) weeds; in particular: *Alopecurus myosuroides* (ALOMY, English name "blackgrass"), *Apera spica-venti, Avena fatua* (AVEFA, English name "wild oats"), *Avena ludoviciana, Avena sterilis, Avena sativa* (English name "oats" (volunteer)), *Brachiaria decumbens, Brachiaria plantaginea, Brachiaria platyphylla* (BRAPP), *Bromus tectorum, Digitaria horizontalis, Digitaria insularis, Digitaria sanguinalis* (DIGSA), *Echinochloa crus-galli* (English name "common barnyard grass", ECHCG), *Echinochloa oryzoides, Echinochloa colona* or *colonum, Eleusine indica, Eriochloa villosa* (English name "woolly cupgrass"), *Leptochloa chinensis, Leptochloa panicoides, Lolium perenne* (LOLPE, English name "perennial ryegrass"), *Lolium multiflorum* (LOLMU, English name "Italian ryegrass"), *Lolium persicum* (English name "Persian darnel"), *Lolium rigidum, Panicum dichotomiflorum* (PANDI), *Panicum miliaceum* (English name "wild proso millet"), *Phalaris minor, Phalaris paradoxa, Poa annua* (POAAN, English name "annual bluegrass"), *Scirpus maritimus, Scirpus juncoides, Setaria viridis* (SETVI, English name "green foxtail"), *Setaria faberi* (SETFA, English name "giant foxtail"), *Setaria glauca, Setaria lutescens* (English name "yellow foxtail"), *Sorghum bicolor*, and/or *Sorghum halepense* (English name "Johnson grass"), and/or *Sorghum vulgare*; and/or volunteer corn (volunteer maize) weeds.

In one embodiment, grassy monocotyledonous weeds to be controlled comprise weeds from the genus: *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum*, and/or volunteer corn (volunteer maize) weeds; in particular: weeds from the genus *Agrostis, Alopecurus, Apera, Avena, Brachiaria, Bromus, Cenchrus, Digitaria, Echinochloa, Eleusine, Eriochloa, Leptochloa, Lolium, Panicum, Phalaris, Poa, Rottboellia, Setaria*, and/or *Sorghum*, and/or volunteer corn (volunteer maize) weeds.

In a further embodiment, the grassy monocotyledonous weeds are "warm-season" (warm climate) grassy weeds; in which case they preferably comprise (e.g. are): weeds from the genus *Brachiaria, Cenchrus, Digitaria, Echinochloa, Eleusine, Eriochloa, Leptochloa, Ottochloa, Panicum, Pennisetum, Phalaris, Rottboellia, Setaria* and/or *Sorghum*, and/or volunteer corn (volunteer maize) weeds. More preferably, the grassy monocotyledonous weeds, e.g. to be controlled and/or growth-inhibited, are "warm-season" (warm climate) grassy weeds comprising (e.g. being): weeds from the genus *Brachiaria, Cenchrus, Digitaria, Echinochloa, Eleusine, Eriochloa, Panicum, Setaria* and/or *Sorghum*, and/or volunteer corn (volunteer maize) weeds.

In another particular embodiment the grassy monocotyledonous weeds, are "cool-season" (cool climate) grassy weeds; in which case they typically comprise weeds from the genus *Agrostis, Alopecurus, Apera, Avena, Bromus, Lolium* and/or *Poa*.

Various aspects and embodiments of the present invention will now be illustrated in more detail by way of example. It will be appreciated that modification of detail may be made without departing from the scope of the invention.

PREPARATION EXAMPLES

Throughout the following examples, $^1$H NMR spectra were recorded at 400 MHz or 500 MHz either on a Varian Unity Inova instrument or Bruker AVANCE-II instrument.

The following abbreviations are used: s=singlet; bs=broad singlet; d=doublet; bd=broad doublet; dd=double doublet; t=triplet, q=quartet; m=multiplet; THF=tetrahydrofuran; EtOAc=ethyl acetate; EtOH=ethanol; DMSO=dimethyl sulfoxide; DPPA=diphenylphosphoryl azide; DMF=N,N-dimethyl formamide; dppf=1,1'-bis(diphenylphosphino)ferrocene; Pd(OAc)$_2$=palladium(II) acetate; Et$_3$N=triethylamine; MeOH=methanol.

Chemical names were generated using the 'Text from structure' feature in Accelrys Draw 4.0.

Example P1 Preparation of Compound A2, tert-butyl N-[2-methyl-5-(3-pyridyl) pyrazol-3-yl]carbamate 1.1 Step 1: Preparation of ethyl 2,4-dioxo-4-(3-pyridyl)butanoate

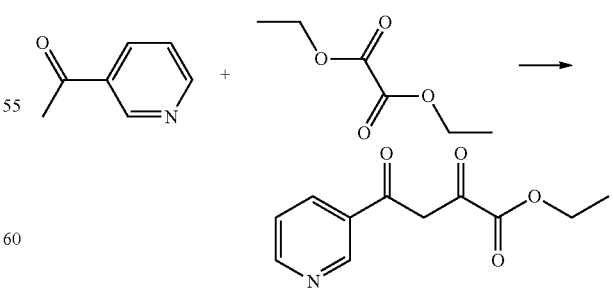

NaH (60% w/w, 9.91 g, 248.0 mmol) was added to a flask charged with dry THF (170 mL). Diethyl oxalate (24.13 g, 165.1 mmol) was added and washed in with dry THF (15 mL). The mixture was heated to reflux, then a solution of 1-(3-pyridyl)ethanone (10.0 g, 82.55 mmol) in THF (15 mL) was added slowly with stirring at reflux. After 15 minutes the mixture was cooled to room temperature and slowly added, with stirring and cooling, to a mixture of 2M HCl (130 mL) in water (375 mL). The resulting mixture was treated with solid NaHCO₃ until slightly basic then extracted three times with EtOAc. The combined organics were washed once with brine, dried (MgSO₄) and concentrated in vacuo to yield a dark brown gum, which solidified on standing.

Mineral oil was removed by washing and decanting with hexane. The solid was dissolved in warm ethanol (350 mL) and treated with decolourising charcoal. After 5 minutes the solution was filtered hot, through celite. The filtrate was concentrated in vacuo to give crude ethyl 2,4-dioxo-4-(3-pyridyl)butanoate (15.0 g) which was used without further purification.

¹H NMR (400 MHz, CDCl₃) δ=9.21 (1H, d), 8.83 (1H, dd), 8.29 (1H, m), 7.46-7.52 (1H, m), 7.08 (1H, s), 4.39-4.46 (2H, q), 1.40-1.46 (3H, t).

1.2 Step 2: Preparation of ethyl 2-methyl-5-(3-pyridyl)pyrazole-3-carboxylate

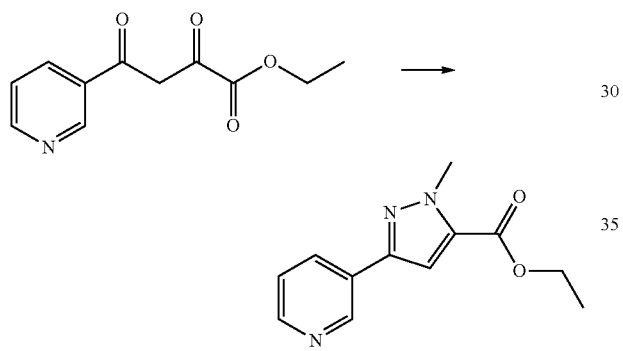

To a flask charged with ethyl 2,4-dioxo-4-(3-pyridyl) butanoate (10.0 g, 45.2 mmol), dissolved in EtOH (120 mL) was added methylhydrazine (2.4 mL, 46.0 mmol) The mixture was heated to reflux for 2.5 hours then left to stand overnight.

The solvent was removed in vacuo and the crude material purified via flash column chromatography on silica gel using an EtOAc/hexane gradient to afford ethyl 2-methyl-5-(3-pyridyl)pyrazole-3-carboxylate (2.52 g).

¹H NMR (400 MHz, CDCl₃) δ=9.02 (1H, m), 8.56 (1H, dd), 8.11 (1H, m), 7.34 (1H, dd), 7.17 (1H, s), 4.39 (2H, q), 4.25 (3H, s), 1.42 (3H, t)

1.3 Step 3: Preparation of ethyl 2-methyl-5-(3-pyridyl)pyrazole-3-carboxylate

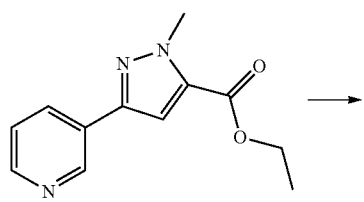

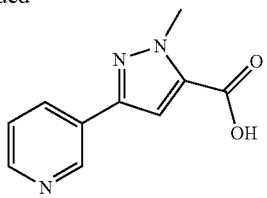

To a flask charged with ethyl 2-methyl-5-(3-pyridyl) pyrazole-3-carboxylate (2.52 g, 10.9 mmol) dissolved in 1,4-dioxane (17 mL), cooled in an ice bath was added NaOH (1.09 g, 27.3 mmol) in water (3.3 mL) drop-wise. The resulting bi-phasic solution was stirred at ambient temperature for 2 hours, after which time water was added portion-wise until homogeneous (13.2 mL).

The reaction mixture was stirred at ambient temperature for a further 2 hours, after which time solvent was concentrated to ca. 50% volume in vacuo and diluted with water (20 mL). The reaction mixture was acidified with 2M HCl (13.5 mL) and the solid precipitate filtered off at the pump, washed with water and air dried overnight to afford 2-methyl-5-(3-pyridyl)pyrazole-3-carboxylic acid (1.70 g) as an off-white solid.

¹H NMR (400 MHz, d₆-DMSO) δ=9.06 (1H, m), 8.53 (1H, dd), 8.20 (1H, d), 7.45 (1H, m), 7.43 (1H, s), 4.15 (3H, s).

1.4 Step 4: Preparation of tert-butyl N-[2-methyl-5-(3-pyridyl)pyrazol-3-yl]carbamate

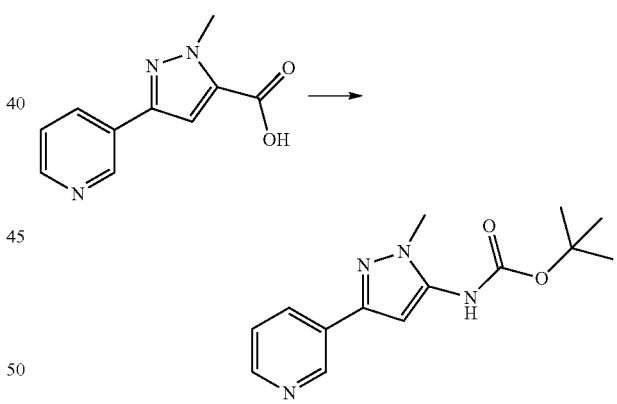

To a flask charged with 2-methyl-5-(3-pyridyl)pyrazole-3-carboxylic acid (1.70 g, 8.34 mmol) suspended in tert-butanol (37 mL) and toluene (37 mL) was added triethylamine (1.18 mL, 8.38 mmol) and DPPA (2.30 g, 8.40 mmol) drop-wise with stirring and the resulting mixture was then heated gradually to reflux. After 4.5 hours at reflux the reaction mixture was allowed to cool and the solvent was removed in vacuo. The residue was purified via flash column chromatography on silica gel using an EtOAc/hexane gradient to afford tert-butyl N-[2-methyl-5-(3-pyridyl)pyrazol-3-yl]carbamate (0.75 g) as a colourless gum.

¹H NMR (400 MHz, CDCl₃) δ=8.98 (1H, bs), 8.53 (1H, bs), 8.05 (1H, m), 7.30 (1H, m), 6.63 (1H, bs), 6.53 (1H, bs), 3.81 (3H, s), 1.53 (9H, s).

Example P2 Preparation of Compound A1, tert-butyl N-methyl-N-[2-methyl-5-(3-pyridyl)pyrazol-3-yl]carbamate

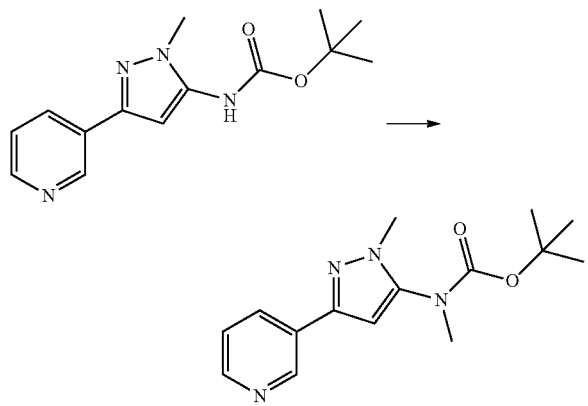

tert-Butyl N-[2-methyl-5-(3-pyridyl)pyrazol-3-yl]carbamate (245 mg, 0.893 mmol) was dissolved in dry DMF (2.5 mL), cooled in an ice bath, then NaH (60% w/w, 42.9 mg, 1.07 mmol) added as a single portion. After 5 minutes the mixture was allowed to warm to ambient temperature for 5 minutes (solution turned brown). The ice bath was reapplied and a solution of MeI (133.1 mg, 0.938 mmol) in dry DMF (0.7 mL) was added dropwise. After 30 minutes the reaction was warmed to ambient temperature and stirred for a further hour.

Reaction was quenched with water (13 mL) containing 2M HCl (89 µL). The mixture was extracted three times with EtOAc, and the combined organics washed twice with brine and then dried (MgSO$_4$). The solvent was concentrated in vacuo and the residue was purified via flash column chromatography on silica gel using an EtOAc/hexane gradient to afford tert-butyl N-methyl-N-[2-methyl-5-(3-pyridyl)pyrazol-3-yl]carbamate (125.0 mg) as an amber gum.

$^1$H NMR (400 MHz, CDCl$_3$) δ=8.97 (1H, d), 8.51-8.56 (1H, m) 8.07 (1H, d), 7.28-7.35 (1H, m), 6.40 (1H, s), 3.75 (3H, s), 3.22 (3H, s), 1.45 (9H, s).

Example P3 Preparation of Compound A3, tert-butyl N-(3-methyl-1-pyrimidin-5-yl-pyrazol-4-yl)carbamate

3.1 Step 1: Preparation of ethyl 3-methyl-1-pyrimidin-5-yl-pyrazole-4-carboxylate

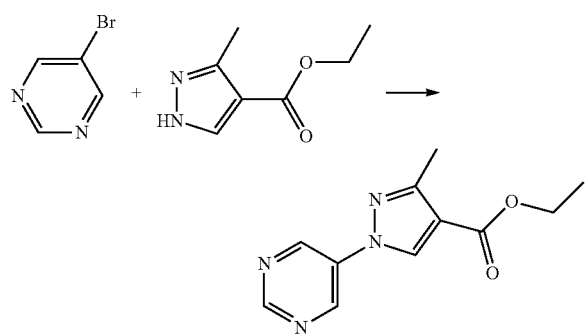

To a flask charged with 5-bromopyrimidine (248 mg, 1.56 mmol) dissolved in 1,4-dioxane (5 mL) was added K$_2$CO$_3$ (359 mg, 2.59 mmol), CuI (124 mg, 0.065 mmol), trans-N,N'-dimethylcyclohexane-1,2-diamine (28.5 mg, 0.195 mmol) and ethyl 3-methyl-1H-pyrazole-4-carboxylate (200 mg, 1.30 mmol). This gave a blue suspension which was heated to 110° C. and stirred overnight.

Overnight the reaction had become dark grey. After cooling, the reaction mixture was poured into EtOAc and water. This was extracted twice with EtOAc. The combined organics were washed with brine and dried (MgSO$_4$), the combined organics were concentrated in vacuo to yield a brown solid which was purified via flash column chromatography on silica gel using an EtOAc/hexane gradient to afford ethyl 3-methyl-1-pyrimidin-5-yl-pyrazole-4-carboxylate (255 mg) as a white solid.

$^1$H NMR (400 MHz, CDCl$_3$) δ=9.18 (1H, s), 9.14 (2H, s), 8.42 (1H, s), 4.35 (2H, q), 2.58 (3H, s), 1.39 (3H, t).

3.2 Step 2: Preparation of 3-methyl-1-pyrimidin-5-yl-pyrazole-4-carboxylic Acid

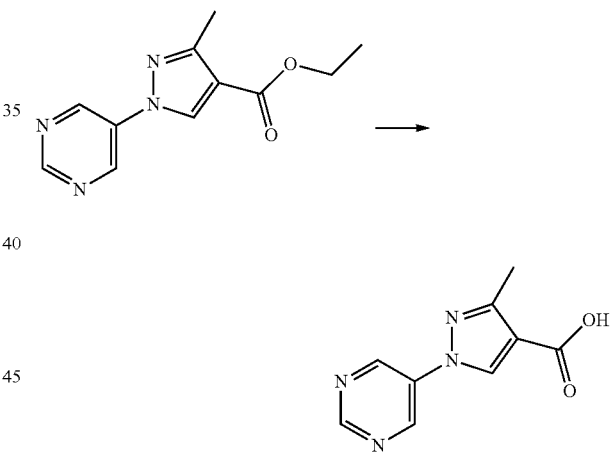

To a flask charged with ethyl 3-methyl-1-pyrimidin-5-yl-pyrazole-4-carboxylate (180 mg, 0.775 mmol) in 1,4-dioxane (3.4 mL) was added NaOH (68.2 mg 1.71 mmol) dissolved in water (1.7 mL) to form a yellowish solution which was stirred at 55° C. overnight.

The reaction mixture was concentrated in vacuo to remove the organics and the aqueous layer was acidified to pH 3 with 1M HCl to give a white solid. The precipitate was filtered off at the pump and washed twice with water, then washed with EtOAc and air-dried to give a 3-methyl-1-pyrimidin-5-yl-pyrazole-4-carboxylic acid (84 mg) as a white solid $^1$H NMR (400 MHz, d6-DMSO) δ=9.35 (2H, s), 9.15 (1H, s), 9.10 (1H, s), 2.42 (3H, s).

3.3 Step 3: Preparation of tert-butyl N-(3-methyl-1-pyrimidin-5-yl-pyrazol-4-yl)carbamate, Compound A3

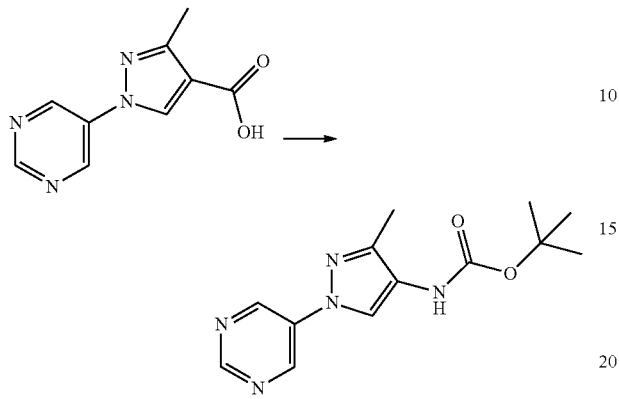

To a flask charged with 3-methyl-1-pyrimidin-5-yl-pyrazole-4-carboxylic acid (0.206 g, 1.01 mmol) and tert-butanol (7 mL) was added triethylamine (0.141 mL, 1.0 mmol) dropwise via syringe. To this was added DPPA (0.219 mL 1.01 mmol) dropwise via syringe and the mixture heated to reflux overnight.

Overnight a white precipitate formed and upon cooling this was filtered off at the pump and the filtrate concentrated in vacuo to leave a yellow residue. This was partitioned between water and EtOAc. The aqueous was extracted with 3 further portions of EtOAc. The combined organics were washed with brine, dried (MgSO$_4$), and evaporated to dryness to give a cream solid (297 mg). The crude product was purified via flash column chromatography on silica gel eluting with an EtOAc/hexane gradient to afford tert-butyl N-(3-methyl-1-pyrimidin-5-yl-pyrazol-4-yl)carbamate as a white solid (64 mg).

$^1$H NMR (400 MHz, CDCl$_3$) δ=9.08 (3H, s), 8.28 (1H, s), 6.17 (1H, s), 2.31 (3H, s), 1.54 (9H, s).

Example P4 Preparation of tert-butyl N-methyl-N-(3-methyl-1-pyrimidin-5-yl-pyrazol-4-yl)carbamate, Compound A5

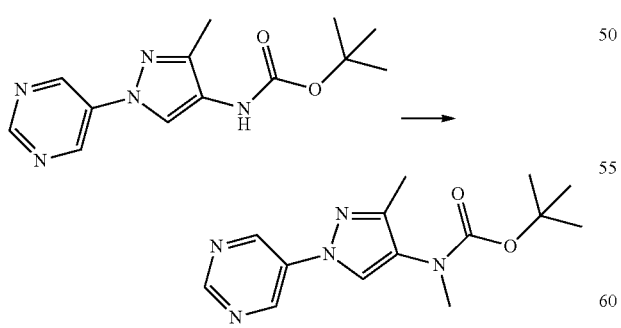

To a flask charged with tert-butyl N-(3-methyl-1-pyrimidin-5-yl-pyrazol-4-yl)carbamate (68.0 mg, 0.25 mmol) dissolved in DMF (1 mL), under nitrogen, and cooled in an ice bath ice, was added NaH (60% w/w 11.0 mg, 0.27 mmol) as a single portion to give a bright yellow solution. The mixture was stirred in an ice bath for 10 minutes then allowed to warm to ambient temperature for 40 minutes. The ice bath was reapplied and MeI (16 µL, 0.26 mmol) was added dropwise via syringe. The reaction was stirred at ambient temperature for 2 hours and quenched with water and extracted twice with Et$_2$O. The combined organics were washed with brine, dried (MgSO$_4$), and concentrated in vacuo to give tert-butyl N-methyl-N-(3-methyl-1-pyrimidin-5-yl-pyrazol-4-yl)carbamate (51 mg) as a white solid.

$^1$H NMR (400 MHz, CDCl$_3$) δ=9.10 (1H, s), 9.06 (2H, s), 7.85 (1H, s), 3.21 (3H, s), 2.28 (3H, s), 1.57 (9H, s).

Example P5 Preparation of isopropyl N-[2-(difluoromethyl)-5-pyrimidin-5-yl-pyrazol-3-yl]carbamate, Compound A58

Step One: Synthesis of methyl pyrimidine-5-carboxylate

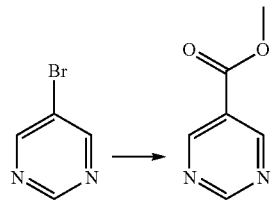

Carbon monoxide gas was introduced to a mixture of 5-bromopyrimidine (15.9 g, 0.1 mol), dppf (2.22 g, 4 mmol), Pd(OAc)$_2$ (448 mg, 2 mmol) and Et$_3$N (20.2 g, 0.2 mol) in MeOH (120 mL) and the internal pressure was increased to 30 bar. The reaction mixture was stirred at 95° C. for about 4 hours, then cooled to room temperature and filtered. The filtrate was concentrated under reduced pressure and the residue was purified by column chromatography on silica gel (eluent: petroleum ether/ethyl acetate=5:1) to provide methyl pyrimidine-5-carboxylate (9.6 g, 70% yield) as a white solid.

$^1$H NMR (400 MHz, CDCl3) δ=9.36 (1H, s), 9.27 (2H, s), 3.98 (3H, s).

Step Two: Synthesis of 3-pyrimidin-5-yl-1H-pyrazol-5-amine

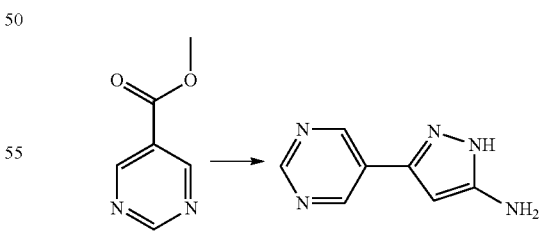

Methyl pyrimidine-5-carboxylate (5.3 g, 38 mmol) was added to a suspension of NaH (2.4 g, 60 mmol) in acetonitrile (1.57 g, 38 mmol) and THF (50 mL), and the mixture was heated under reflux overnight. The precipitate was filtered off and washed with diethyl ether to give 3-oxo-3-pyrimidin-5-yl-propanenitrile sodium salt as a yellow solid, which was directly used in the next step without further purification.

A mixture of the 3-oxo-3-pyrimidin-5-yl-propanenitrile sodium salt (5 g), hydrazine hydrochloride (3.0 g, 44 mmol), acetic acid (1.7 g, 30 mmol) and hydrochloric acid (0.2 mL, 1M) in EtOH (100 mL) was heated under reflux for 3 hours. The reaction mixture was then cooled to room temperature and concentrated under vacuum. The residue was purified by column chromatography on silica gel to give the 5-pyrimidin-5-yl-1H-pyrazol-3-amine (1.5 g) as a yellow solid.

$^1$H NMR (400 MHz, DMSO-d$_6$) δ=11.84 (1H, bs), 9.03 (3H, s), 5.85 (1H, s), 5.09 (2H, bs).

Step Three: Synthesis of 2-(difluoromethyl)-5-pyrimidin-5-yl-pyrazol-3-amine

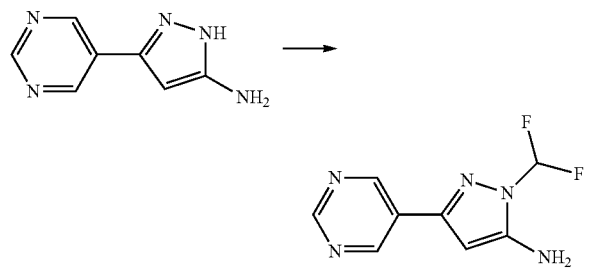

CHClF$_2$ (26.66 g, 310 mmol) was introduced to a mixture of 5-pyrimidin-5-yl-1H-pyrazol-3-amine (5 g, 31 mmol) and KOH (8.68 g, 155 mmol) in dioxane (30 mL) and water (20 mL) in an autoclave. The reaction mixture was heated at 100° C. and the internal pressure increased to 15 bar. After stirring for 4 h, the reaction mixture was cooled to room temperature, diluted with water (50 mL) and extracted three times with EtOAc. The combined extracts were dried over anhydrous sodium sulfate, concentrated under vacuum and purified by flash chromatography on silica gel (eluent petroleum ether/ethyl acetate 3:1) to give 1-(difluoromethyl)-5-pyrimidin-5-yl-pyrazol-3-amine (260 mg) and the desired 2-(difluoromethyl)-5-pyrimidin-5-yl-pyrazol-3-amine (260 mg) as a yellow solid.

$^1$H NMR (400 MHz, DMSO-d$_6$) δ=9.17 (1H, s), 9.14 (2H, s), 7.65 (1H, t), 6.19 (2H, s), 5.97 (1H, s).

Step Four: Synthesis of isopropyl N-[2-(difluoromethyl)-5-pyrimidin-5-yl-pyrazol-3-yl]carbamate, Compound A58

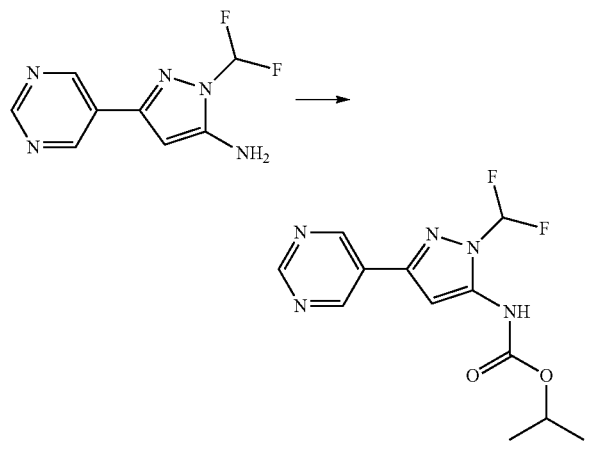

To a vial charged with 2-(difluoromethyl)-5-pyrimidin-5-yl-pyrazol-3-amine (100 mg, 0.47 mmol) was added dichloromethane (7 mL) with pyridine (94 mg, 1.184 mmol) and the mixture stirred for 5 minutes. Isopropyl chloroformate (1M in toluene) (0.59 mmol, 0.59 mL) was added dropwise and the mixture allowed to stir overnight. The sample was concentrated in vacuo and pre-adsorbed onto silica gel prior to purification via flash column chromatography using an EtOAc/Hexanes gradient to give the desired product as a thick gum (82 mg).

$^1$H NMR (400 MHz, CDCl$_3$) δ=9.22 (1H, s), 9.16 (2H, s), 7.28 (1H, t), 7.20 (1H, bs), 6.92 (1H, bs), 5.05 (1H, m), 1.30 (6H, d).

Example P6 Preparation of isopropyl N-[2-(difluoromethyl)-5-pyrimidin-5-yl-pyrazol-3-yl]-N-methyl-carbamate, Compound A59

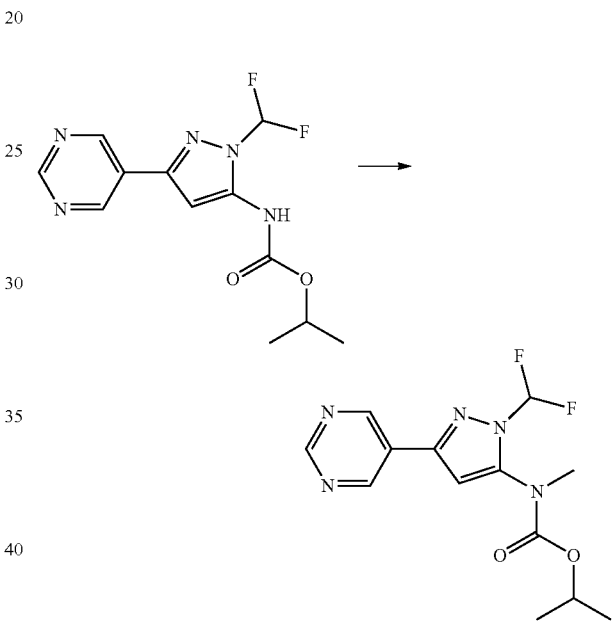

To a flask charged with isopropyl N-[2-(difluoromethyl)-5-pyrimidin-5-yl-pyrazol-3-yl]carbamate (82 mg, 0.276 mmol) was added DMF (5 mL) and stirred until homogeneous. The mixture was cooled to 0° C. (ice bath) and sodium hydride (65% w/w in mineral oil) (12 mg, 0.29 mmol) was added as a single portion. After 5 minutes the mixture was removed from the ice bath and stirred at ambient for a further 5 minutes. The flask was then re-cooled to 0° C. (ice bath) and iodomethane (42 mg, 0.295 mmol, 0.0180 mL) was added dropwise. After 10 minutes the mixture was allowed to warm to ambient and stirred for a further 30 minutes. The mixture was quenched with 2M HCl (500 μL) and concentrated in vacuo. The resulting residue was then dissolved in CH$_2$Cl$_2$ and pre-adsorbed onto silica gel prior to purification via flash column chromatography on silica gel using an EtOAc/hexanes gradient. This gave the desired compound as a white solid (44 mg).

$^1$H NMR (400 MHz, CDCl$_3$) δ=9.22 (1H, s), 9.12 (2H, s), 7.14 (1H, t), 6.60 (1H, s), 4.98 (1H, m), 3.27 (3H, s), 1.22 (6H, bd).

Example P7 Preparation of tert-butyl N-[3-chloro-1-(3-pyridyl)pyrazol-4-yl]-N-methyl-carbamate, Compound A60 tert-Butyl N-[3-chloro-1-(3-pyridyl)pyrazol-4-yl] carbamate was Prepared According to Procedures in U.S. Pat. No. 8,901,153

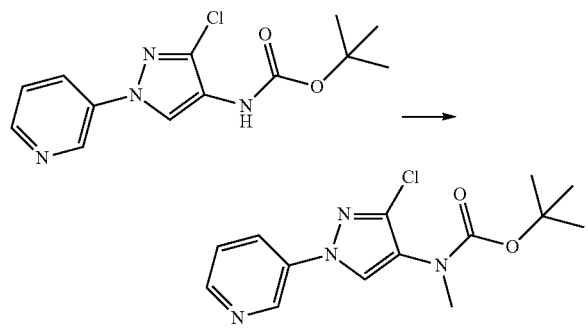

To a flask charged with tert-butyl N-[3-chloro-1-(3-pyridyl)pyrazol-4-yl]carbamate (200 mg, 0.69 mmol) in DMF (6 mL) and cooled in an ice bath was added sodium hydride (60% w/w in oil) (30 mg, 0.75 mmol) portionwise over ca. 5 mins. The reaction mixture turned a deep yellow colour over this time and a fine precipitate could be observed. The mixture was then warmed to ambient and stirred for 5 minutes. The ice bath was re-applied and iodomethane (212 mg, 1.49 mmol, 92 µL) was added dropwise. The mixture was stirred in the ice bath for 2 hours, then allowed to warm to ambient and diluted with brine (5 mL). The reaction was extracted with EtOAc (3×10 mL) and the combined organics were concentrated in vacuo and then loaded onto a $SiO_2$ column then purified via flash column chromatography on silica gel (eluted with EtOAc/hexane gradient) to give the desired compound as a colourless oil (102 mg).

$^1$H NMR (400 MHz, $CDCl_3$) δ=8.92 (1H, d), 8.57 (1H, d), 8.07 (1H, m), 7.90 (1H, bs), 7.42 (1H, m), 3.22 (3H, s), 1.39 (9H, s).

Further examples of the invention were made in an analogous way using the methods described above in Examples P1 to P7 with respect to compounds A1, A2, A3, A5, A58, A59 and A60. Table 2 below, summarises the physical data for such compounds.

TABLE 2

Compounds made by the methods described above.

| Cmpd | Structure | Physical Data 1H NMR (400 MHz, $CDCl_3$) unless stated |
|---|---|---|
| A1 | 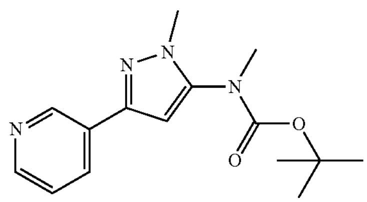 [SMILES: CN(C(=O)OC(C)(C)C)c1cc(-c2cccnc2)nn1C] | 8.97 (1H, d), 8.51-8.56 (1H, m) 8.07 (1H, d), 7.28-7.35 (1H, m), 6.40 (1H, s), 3.75 (3H, s), 3.22 (3H, s), 1.45 (9H, s) |
| A2 | 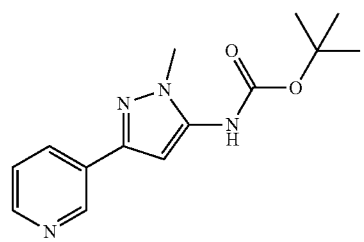 [SMILES: Cn1nc(-c2cccnc2)cc1NC(=O)OC(C)(C)C] | 8.98 (1H, bs), 8.53 (1H, bs), 8.05 (1H, m), 7.30 (1H, m), 6.63 (1H, br. s), 6.53 (1H, bs), 3.81 (3H, s), 1.53 (9H, s), |
| A3 | 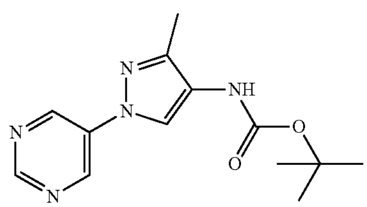 [SMILES: Cc1nn(-c2cncnc2)cc1NC(=O)OC(C)(C)C] | 9.08 (3H, s), 8.28 (1H, s), 6.17 (1H, s), 2.31 (3H, s), 1.54 (9H, s) |
| A4 | 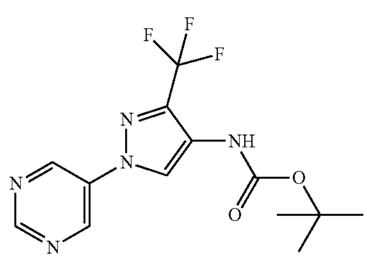 [SMILES: CC(C)(C)OC(=O)Nc1cn(-c2cncnc2)nc1C(F)(F)F] | 9.20 (1H, s), 9.04 (2H, s), 8.59 (1H, s), 6.62 (1H, bs), 1.55 (9H, s) |

TABLE 2-continued

Compounds made by the methods described above.

| Cmpd | Structure | Physical Data 1H NMR (400 MHz, CDCl$_3$) unless stated |
| --- | --- | --- |
| A5 | 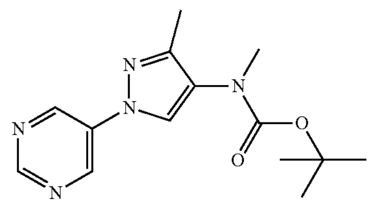 [SMILES: Cc1nn(-c2cncnc2)cc1N(C)C(=O)OC(C)(C)C] | 9.10 (1H, s), 9.06 (2H, s), 7.85 (1H, s), 3.21 (3H, s), 2.28 (3H, s), 1.57 (9H, s) |
| A6 | 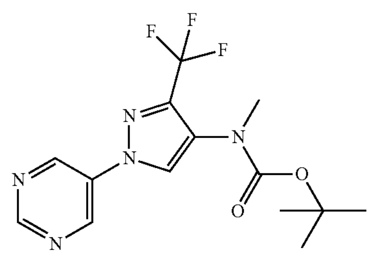 [SMILES: CN(C(=O)OC(C)(C)C)c1cn(-c2cncnc2)nc1C(F)(F)F] | 9.24 (2H, s), 9.14 (1H, s), 8.01 (1H, s), 3.20 (3H, s), 1.40 (9H, s) |
| A7 | 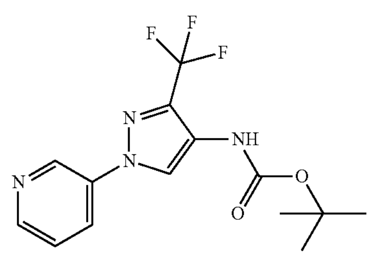 [SMILES: CC(C)(C)OC(=O)Nc1cn(-c2cccnc2)nc1C(F)(F)F] | 9.03 (1H, d), 8.62 (1H, dd), 8.55 (1H, s), 8.04 (1H, dd), 7.41 (1H, dd), 6.53 (1H, br. s), 1.52 (9H, bs) |
| A8 | 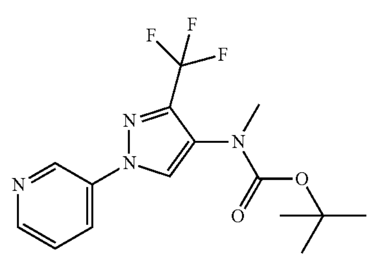 [SMILES: CN(C(=O)OC(C)(C)C)c1cn(-c2cccnc2)nc1C(F)(F)F] | 8.91 (1H, d), 8.52 (1H, d), 8.04 (1H, m), 7.89 (1H, bs), 7.41 (1H, dd), 3.22 (3H, s), 2.29 (3H, s), 1.47 (9H, bs) |
| A10 | 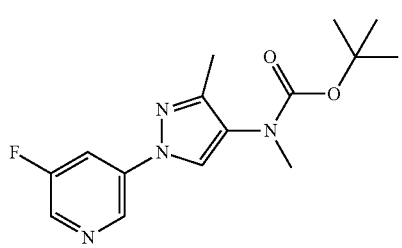 [SMILES: Cc1nn(-c2cncc(F)c2)cc1N(C)C(=O)OC(C)(C)C] | 8.71 (1H, s), 8.36 (1H, d), 7.90-7.73 (2H, m), 3.20 (3H, s), 2.27 (3H, s), 1.46 (9H, bs) |
| A14 | 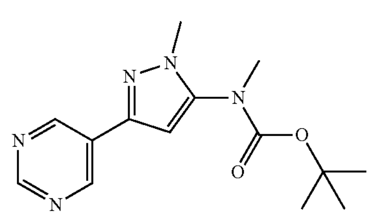 [SMILES: CN(C(=O)OC(C)(C)C)c1cc(-c2cncnc2)nn1C] | 9.13 (1H, s), 9.10 (2H, s), 6.43 (1H, s), 3.75 (3H, s), 3.21 (3H, s), 2.22 (3H, s), 1.45 (9H, s) |

TABLE 2-continued
Compounds made by the methods described above.
| Cmpd | Structure | Physical Data 1H NMR (400 MHz, CDCl$_3$) unless stated |
|---|---|---|
| A16 | 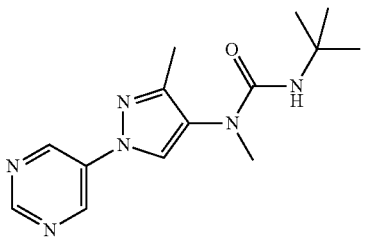 [SMILES: Cc1nn(-c2cncnc2)cc1N(C)C(=O)NC(C)(C)C] | 9.14 (1H, s), 9.12 (2H, s), 8.02 (1H, s), 4.36 (1H, s), 3.18 (3H, s), 2.29 (3H, s), 1.31 (9H, s) |
| A19 | 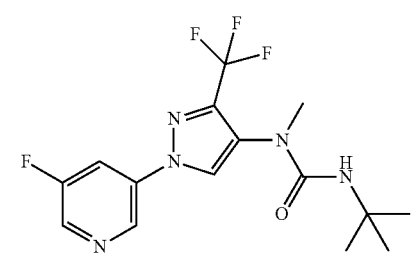 [SMILES: CN(C(=O)NC(C)(C)C)c1cn(-c2cncc(F)c2)nc1C(F)(F)F] | 8.82 (1H, d), 8.54 (1H, d), 8.12 (1H, d), 7.94 (1H, m), 3.18 (3H, s), 1.30 (9H, s) |
| A25 | 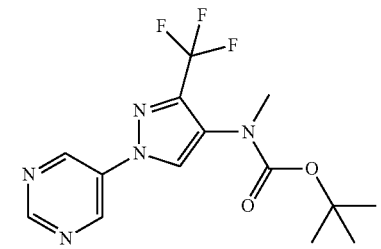 [SMILES: CN(C(=O)OC(C)(C)C)c1cn(-c2cncnc2)nc1C(F)(F)F] | 9.24 (2H, s), 9.14 (1H, s), 8.01 (1H, s), 3.20 (3H, s), 1.40 (9H, s) |
| A27 | 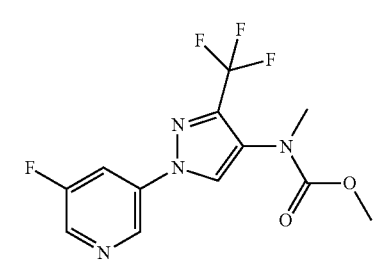 [SMILES: COC(=O)N(C)c1cn(-c2cncc(F)c2)nc1C(F)(F)F] | 8.79 (1H, d), 8.52 (1H, d), 8.01 (1H, br. s), 7.92 (1H, m), 3.70 (3H, bs), 3.26 (3H, s) |
| A39 | 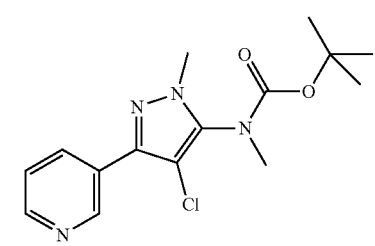 [SMILES: CN(C(=O)OC(C)(C)C)c1c(Cl)c(-c2cccnc2)nn1C] | 9.17 (1H, bs), 8.63-8.55 (1H, m), 8.20 (1H, d), 7.40-7.31 (1H, m), 3.76 (3H, s), 3.22 (3H, s), 1.61-1.35 (9H, m) |
| A43 | 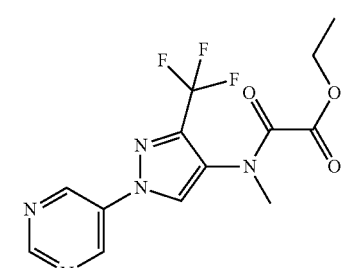 | 9.28 (1H, s), 9.16 (2H, s), 8.22 (1H, s), 4.12 (2H, q), 3.32 (3H, s), 1.13 (3H, t) |

TABLE 2-continued

Compounds made by the methods described above.

| Cmpd | Structure | Physical Data 1H NMR (400 MHz, CDCl$_3$) unless stated |
|---|---|---|
| A44 | 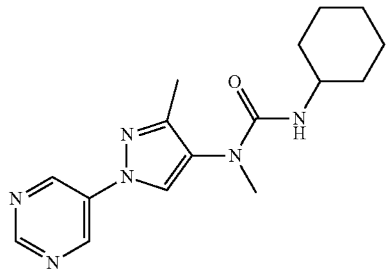 [SMILES: Cc1nn(-c2cncnc2)cc1N(C)C(=O)NC1CCCCC1] | 9.19-9.05 (3H, m), 7.99 (1H, s), 4.31 (1H, d), 3.76-3.53 (1H, m), 3.21 (3H, s), 2.28 (3H, s), 1.96-1.84 (2H, m), 1.72-1.53 (3H, m), 1.42-1.25 (3H, m), 1.11-0.93 (3H, m) |
| A45 | 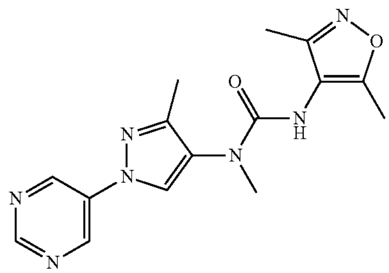 [SMILES: Cc1nn(-c2cncnc2)cc1N(C)C(=O)Nc1c(C)noc1C] | 9.20 (3H, bs), 8.13 (1H, s), 5.68 (1H, s), 3.30 (3H, s), 2.40 (3H, s), 2.29 (3H, s), 2.16 (3H, s) |
| A46 | 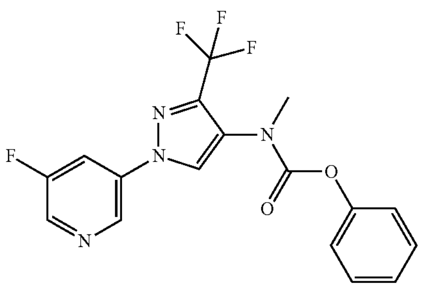 [SMILES: CN(C(=O)Oc1ccccc1)c1cn(-c2cncc(F)c2)nc1C(F)(F)F] | 8.80 (1H, bs), 8.52 (1H, bs), 8.14 (1H, s), 7.91 (1H, d), 7.33 (2H, t), 7.05 (1H, d), 7.24-6.98 (1H, m), 3.34 (3H, s) |
| A47 | 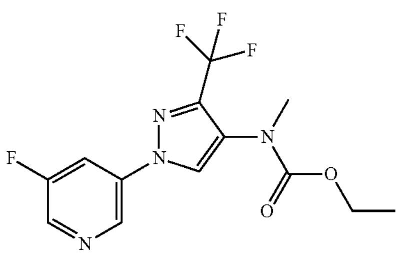 [SMILES: CCOC(=O)N(C)c1cn(-c2cncc(F)c2)nc1C(F)(F)F] | 8.79 (1H, s), 8.51 (1H, d), 8.14-7.96 (1H, m), 7.92 (1H, d), 4.16 (2H, bs), 3.25 (3H, s), 1.38-1.11 (3H, m) |
| A48 | 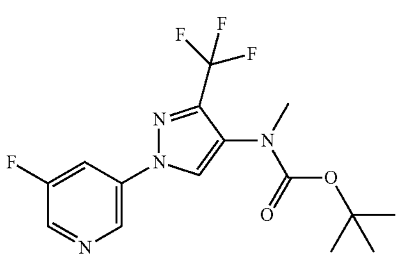 [SMILES: CN(C(=O)OC(C)(C)C)c1cn(-c2cncc(F)c2)nc1C(F)(F)F] | 8.79 (1H, d), 8.51 (1H, d), 8.02 (2H, s), 3.20 (3H, s), 1.41 (9H, bs) |
| A49 | 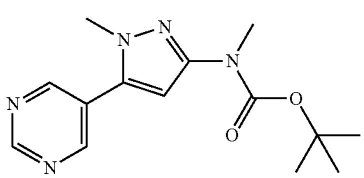 [SMILES: CN(C(=O)OC(C)(C)C)c1cc(-c2cncnc2)n(C)n1] | 9.26 (1H, s), 8.83 (2H, s), 6.70 (1H, br s), 3.82 (3H, s), 3.38 (3H, s), 2.22 (3H, s), 1.54 (9H, s) |

TABLE 2-continued

Compounds made by the methods described above.

| Cmpd | Structure | Physical Data 1H NMR (400 MHz, CDCl$_3$) unless stated |
|---|---|---|
| A51 | 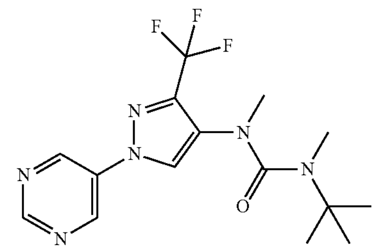 [SMILES: CN(C(=O)N(C)C(C)(C)C)c1cn(-c2cncnc2)nc1C(F)(F)F] | 9.10 (1H, s), 9.06 (2H, s), 7.80 (1H, s), 3.12 (3H, s), 2.60 (3H, s), 2.29 (3H, s), 1.36 (9H, s) |
| A52 | 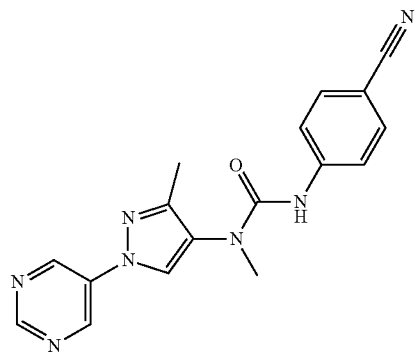 [SMILES: Cc1nn(-c2cncnc2)cc1N(C)C(=O)Nc1ccc(C#N)cc1] | 9.17-9.09 (3H, m), 8.09 (1H, s), 7.55-7.47 (4H, m), 6.80 (1H, s), 3.30 (3H, s), 2.33 (3H, s) |
| A53 | 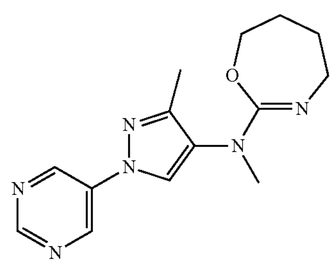 [SMILES: Cc1nn(-c2cncnc2)cc1N(C)C1=NCCCCO1] | 9.17-8.97 (3H, m), 7.86 (1H, s), 3.23-3.04 (7H, m), 2.27 (3H, s), 1.82-1.69 (4H, m) |
| A54 | 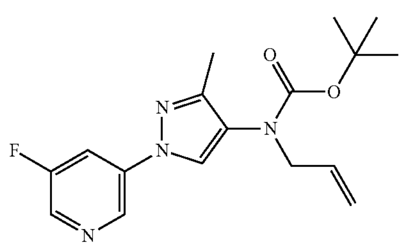 [SMILES: C=CCN(C(=O)OC(C)(C)C)c1cn(-c2cncc(F)c2)nc1C] | 8.77 (1H, s), 8.50 (1H, d), 7.91 (2H, m), 5.99-5.73 (1H, m), 5.26-5.03 (2H, m), 4.16-4.04 (2H, m), 1.41 (9H, bs) |
| A55 | 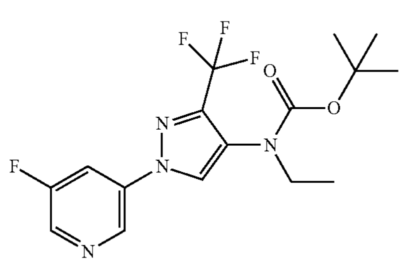 [SMILES: CCN(C(=O)OC(C)(C)C)c1cn(-c2cncc(F)c2)nc1C(F)(F)F] | 8.80 (1H, s), 8.50 (1H, d), 8.06-7.85 (2H, m), 3.60 (2H, q), 1.40 (9H, bs), 1.17 (3H, t) |

TABLE 2-continued

Compounds made by the methods described above.

| Cmpd | Structure | Physical Data 1H NMR (400 MHz, CDCl₃) unless stated |
|---|---|---|
| A56 | 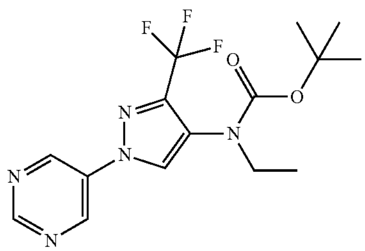 [SMILES: CCN(C(=O)OC(C)(C)C)c1cn(-c2cncnc2)nc1C(F)(F)F] | 9.25 (1H, s), 9.15 (2H, s), 8.00 (1H, s), 3.60 (2H, q), 1.45 (9H, s), 1.20 (3H, t) |
| A57 | 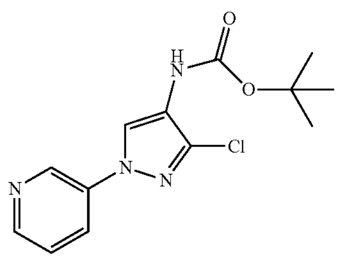 [SMILES: CC(C)(C)OC(=O)Nc1cn(-c2cccnc2)nc1Cl] | 8.98 (1H, d), 8.50-8.46 (2H, m), 8.18 (1H, dd), 7.53 (1H, dd), 4.62 (1H, br), 1.53 (9H, s) |
| A58 | 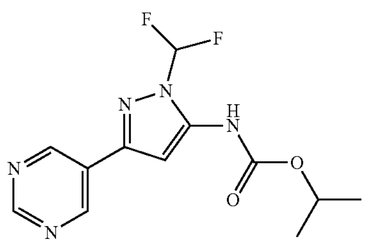 [SMILES: CC(C)OC(=O)Nc1cc(-c2cncnc2)nn1C(F)F] | 9.22 (1H, s), 9.16 (2H, s), 7.28 (1H, t), 7.20 (1H, bs), 6.92 (1H, bs), 5.05 (1H, m), 1.30 (6H, d) |
| A59 | 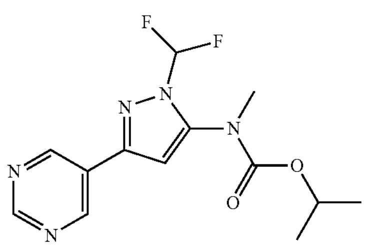 [SMILES: CC(C)OC(=O)N(C)c1cc(-c2cncnc2)nn1C(F)F] | 9.22 (1H, s), 9.12 (2H, s), 7.14 (1H, t), 6.60 (1H, s), 4.98 (1H, m), 3.27 (3H, s), 1.22 (6H, bd) |
| A60 | 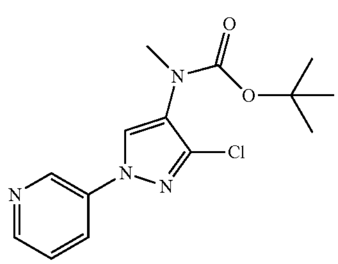 [SMILES: CN(C(=O)OC(C)(C)C)c1cn(-c2cccnc2)nc1Cl] | 8.92 (1H, d), 8.57 (1H, d), 8.07 (1H, m), 7.90 (1H, bs), 7.42 (1H, m), 3.22 (3H, s), 1.39 (9H, s) |

Biologicial Examples

B1 Pre-Emergence Herbicidal Activity

Seeds of a variety of test species were sown in standard soil in pots: *Triticum aestivium* (TRZAW), *Oryza sativa* (ORYSA), *Avena fatua* (AVEFA), *Alopecurus myosuroides* (ALOMY), *Echinochloa crus-galli* (ECHCG), *Lolium perenne* (LOLPE). After cultivation for one day (pre-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown below in Table 3.

TABLE 3

Control of weed species by compounds of formula (I) after pre-emergence application

| Compound | Rate (g/ha) | ECHCG | ORYSA | ALOMY | AVEFA | LOLPE | TRZAW |
|---|---|---|---|---|---|---|---|
| A1  | 1000 | 3 | 1 | 0 | 1 | 1 | 0 |
| A3  | 500  | 4 | 1 | 0 | 0 | 0 | 1 |
| A4  | 1000 | 4 | 1 | 0 | 1 | 0 | 0 |
| A5  | 1000 | 5 | 2 | 1 | 4 | 1 | 4 |
| A6  | 1000 | 5 | 2 | 0 | 3 | 1 | 0 |
| A7  | 500  | 2 | 1 | 0 | 0 | 0 | 0 |
| A8  | 1000 | 3 | 0 | 0 | 1 | 1 | 0 |
| A10 | 1000 | 4 | 1 | 0 | 2 | 1 | 0 |
| A14 | 1000 | 3 | 0 | 1 | 3 | 0 | 1 |
| A16 | 1000 | 2 | 1 | 1 | 1 | 1 | 1 |
| A19 | 1000 | 2 | 0 | 0 | 0 | 1 | 0 |
| A27 | 1000 | 2 | 0 | 0 | 0 | 0 | 0 |
| A39 | 1000 | 3 | 1 | 0 | 4 | 0 | 0 |
| A44 | 1000 | 1 | 1 | 0 | 1 | 1 | 1 |
| A46 | 1000 | 0 | 0 | 0 | 0 | 0 | 0 |
| A47 | 1000 | 1 | 0 | 0 | 0 | 0 | 0 |
| A48 | 1000 | 3 | 1 | 1 | 0 | 1 | 1 |
| A51 | 1000 | 1 | 1 | 0 | 0 | 0 | 0 |
| A52 | 1000 | 0 | 0 | 0 | 0 | 0 | 0 |
| A53 | 1000 | 0 | 0 | 0 | 0 | 0 | 0 |
| A54 | 1000 | 0 | 0 | 0 | 0 | 0 | 0 |
| A55 | 1000 | 0 | 0 | 0 | 0 | 0 | 0 |
| A56 | 1000 | 1 | 0 | 0 | 0 | 0 | 0 |

B1a Pre-Emergence Herbicidal Activity

Seeds of a variety of test species were sown in standard soil in pots: *Amaranthus retroflexus* (AMARE), *Setaria faberi* (SETFA), *Zea mays* (ZEAMX), *Abutilon threophrasti* (ABUTH), *Echinochloa crus-galli* (ECHCG), *Lolium perenne* (LOLPE). After cultivation for one day (pre-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown below in Table 4

B2 Post-Emergence Herbicidal Activity

Seeds of a variety of test species were sown in standard soil in pots: *Triticum aestivium* (TRZAW), *Oryza sativa* (ORYSA), *Avena fatua* (AVEFA), *Alopecurus myosuroides* (ALOMY), *Echinochloa crus-galli* (ECHCG), *Lolium perenne* (LOLPE). After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Table 5 below.

TABLE 4

Control of weed species by compounds of formula (I) after pre-emergence application

| Compound | Rate (g/ha) | LOLPE | AMARE | SETFA | ECHCG | ZEAMX | ABUTH |
|---|---|---|---|---|---|---|---|
| A43 | 1000 | 0 | 0 | 0 | 0 | 0 | 0 |
| A45 | 1000 | 0 | 0 | 0 | 0 | 0 | 0 |
| A57 | 1000 | 0 | 0 | 0 | 0 | 1 | 0 |
| A58 | 1000 | 0 | 0 | 2 | 1 | 0 | 0 |
| A59 | 1000 | 0 | 0 | 3 | 2 | 2 | 0 |
| A60 | 1000 | 0 | 1 | 4 | 2 | 2 | 0 |

TABLE 5

Control of weed species by compounds of formula (I) after post-emergence application

| Compound | Rate (g/ha) | ECHCG | ORYSA | ALOMY | AVEFA | LOLPE | TRZAW |
|---|---|---|---|---|---|---|---|
| A1  | 1000 | 5 | 4 | 3 | 1 | 1 | 1 |
| A3  | 500  | 5 | 1 | 2 | 4 | 2 | 1 |
| A4  | 1000 | 5 | 2 | 1 | 1 | 1 | 1 |
| A5  | 1000 | 5 | 5 | 4 | 0 | 2 | 2 |
| A6  | 1000 | 5 | 5 | 3 | 1 | 1 | 1 |
| A7  | 500  | 4 | 1 | 2 | 2 | 1 | 0 |
| A8  | 1000 | 4 | 2 | 1 | 0 | 0 | 1 |
| A10 | 1000 | 4 | 1 | 1 | 3 | 1 | 0 |
| A14 | 1000 | 4 | 0 | 1 | 4 | 3 | 1 |
| A16 | 1000 | 4 | 0 | 1 | 3 | 2 | 1 |
| A19 | 1000 | 4 | 0 | 1 | 1 | 1 | 0 |
| A27 | 1000 | 4 | 1 | 0 | 3 | 2 | 1 |
| A39 | 1000 | 4 | 1 | 2 | 1 | 3 | 0 |
| A44 | 1000 | 1 | 0 | 1 | 3 | 2 | 0 |
| A46 | 1000 | 2 | 0 | 0 | 2 | 1 | 0 |
| A47 | 1000 | 4 | 0 | 1 | 2 | 0 | 1 |
| A48 | 1000 | 4 | 1 | 1 | 3 | 2 | 1 |
| A51 | 1000 | 2 | 0 | 1 | 2 | 1 | 2 |
| A52 | 1000 | 0 | 0 | 0 | 0 | 0 | 0 |
| A53 | 1000 | 0 | 0 | 0 | 0 | 1 | 0 |
| A54 | 1000 | 1 | 0 | 1 | 1 | 1 | 0 |
| A55 | 1000 | 0 | 0 | 0 | 0 | 0 | 0 |
| A56 | 1000 | 1 | 0 | 1 | 1 | 0 | 1 |

B2a Post-Emergence Herbicidal Activity

Seeds of a variety of test species were sown in standard soil in pots: *Amaranthus retroflexus* (AMARE), *Setaria faberi* (SETFA), *Zea mays* (ZEAMX), *Abutilon threophrasti* (ABUTH), *Echinochloa crus-galli* (ECHCG), *Lolium perenne* (LOLPE). After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/I water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Table 6 below.

TABLE 6

Control of weed species by compounds of formula (I) after post-emergence application

| Compound | Rate (g/ha) | LOLPE | AMARE | SETFA | ECHCG | ZEAMX | ABUTH |
|---|---|---|---|---|---|---|---|
| A43 | 1000 | 0 | 1 | 1 | 1 | 2 | 2 |
| A45 | 1000 | 0 | 0 | 0 | 0 | 0 | 0 |
| A57 | 1000 | 1 | 1 | 3 | 2 | 2 | 1 |
| A58 | 1000 | 1 | 0 | 3 | 1 | 1 | 0 |
| A59 | 1000 | 0 | 0 | 3 | 1 | 2 | 0 |
| A60 | 1000 | 2 | 3 | 4 | 4 | 3 | 2 |

The invention claimed is:

1. A method, comprising:
   applying, to a weed or to the locus thereof, a controlling amount of at least 50 g/ha of a compound of formula (I),

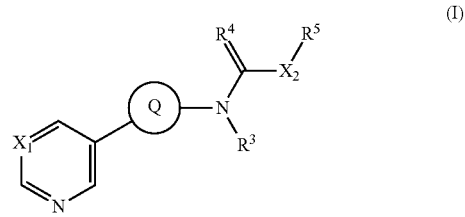

or a salt or N-oxide thereof, wherein Q is a ring system selected from

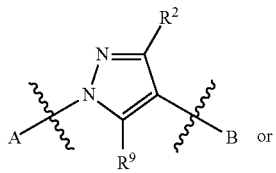
(Q1)

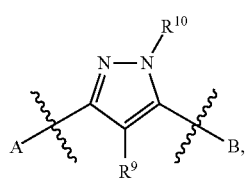
(Q2)

wherein A denotes the point of attachment to the heteroaryl ring, and B denotes the point of attachment to the nitrogen atom;
$X_1$ is N or $CR^1$;
$R^1$ is hydrogen or halogen;
$R^2$ is hydrogen, halogen, $C_1$-$C_6$ alkyl, or $C_1$-$C_6$haloalkyl;
$R^3$ is hydrogen $C_1$-$C_6$alkyl, or $C_2$-$C_6$ alkenyl;
$R^4$ is O or S;
$X_2$ is O, S, or $NR^8$;
$R^5$ is hydrogen, $C_1$-$C_6$alkyl, $C_3$-$C_{10}$cycloalkyl, $C_1$-$C_6$haloalkyl, $C_6$-$C_{10}$aryl or $C_6$-$C_{10}$aryl substituted by 1 to 3 groups independently selected from halogen, cyano, $C_1$-$C_3$ alkyl, and $C_1$-$C_3$ haloalkyl, or $C_3$-$C_{10}$heterocyclyl or $C_3$-$C_{10}$heterocyclyl substituted by 1 to 3 groups independently selected from halogen, cyano, $C_1$-$C_3$ alkyl, and $C_1$-$C_3$ haloalkyl;
or $R^3$ and $R^8$ together with the atoms to which they are attached form a saturated or partially unsaturated 5-9 membered ring system optionally comprising 1 to 3 heteroatoms independently selected from S, O and N and optionally substituted with 1 to 3 groups independently selected from halogen or $C_1$-$C_6$ alkyl;
$R^8$ is hydrogen or $C_1$-$C_6$alkyl;
$R^9$ is hydrogen or halogen; and
$R^{10}$ is hydrogen, $C_1$-$C_6$ alkyl, or $C_1$-$C_6$ haloalkyl;
with proviso that when Q is Q1, $X_2$ is O or S, and $R^5$ is tert-butyl, $R^2$ is not hydrogen, methyl, or chlorine; and wherein the proviso excludes a compound selected from the group consisting of:

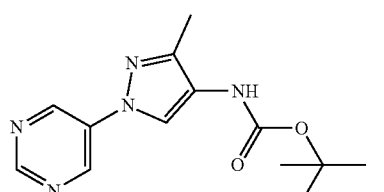
,

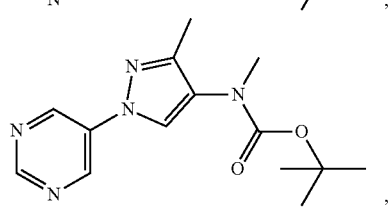
,

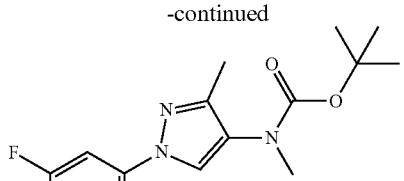

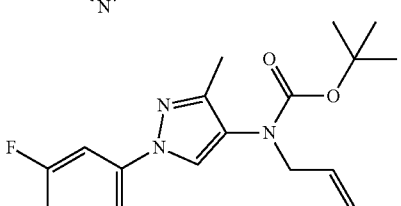
, and

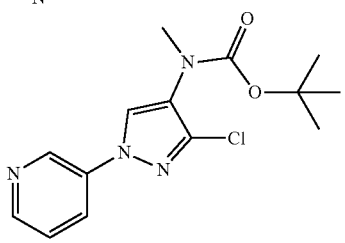
.

2. The method of claim 1, wherein $R^5$ is $C_1$-$C_6$alkyl.
3. The method of claim 2, wherein $R^5$ is tert-butyl.
4. The method of claim 3, wherein $R^4$ is O and $X_2$ is O.
5. The method of claim 1, wherein Q is Q1.
6. The method of claim 1, wherein Q is Q2.
7. The method of claim 1, wherein the controlling amount is 50 to 1000 g/ha.
8. The method of claim 7, wherein applying is to the weed.
9. The method of claim 8, further comprising identifying the weed prior to the applying to the weed.
10. The method of claim 9, wherein the controlling amount is a killing amount.
11. The method of claim 9, wherein the weed is selected from the group consisting of *Brachiaria, Cenchrus, Digitaria, Echinochloa, Eleusine, Eriochloa, Panicum, Setaria, Sorghum, Agrostis, Alopecurus, Apera, Avena, Bromus, Lolium* and *Poa*.
12. The method of claim 9, wherein the weed is *Echinochloa crus-galli*.
13. The method of claim 9, wherein the weed is *Oryza sativa*.
14. The method of claim 9, wherein the weed is *Avena fatua*.
15. The method of claim 9, wherein the weed is *Alopecurus myosuroides*.
16. The method of claim 9, wherein the compound of formula (I) is in a formulation.
17. The method of claim 16, wherein the formulation further comprises at least one additional pesticide selected from the group consisting of an herbicide and herbicide safener.
18. The method of claim 17, wherein when the at least one additional pesticide is an herbicide, the herbicide is selected from the group consisting of: acetochlor, acifluorfen, acifluorfen-sodium, aclonifen, acrolein, alachlor, alloxydim, ametryn, amicarbazone, amidosulfuron, aminopyralid, amitrole, anilofos, asulam, atrazine, azafenidin, azimsulfuron, BCPC, beflubutamid, benazolin, bencarbazone, benfluralin, benfuresate, bensulfuron, bensulfuron-methyl, bensulide, bentazone, benzfendizone, benzobicyclon, benzofenap, bicyclopyrone, bifenox, bilanafos, bispyribac, bispyribac-sodium, borax, bromacil, bromobutide, bromoxynil, butachlor, butamifos, butralin, butroxydim, butylate, cacodylic acid, calcium chlorate, cafenstrole, carbetamide, carfentrazone, carfentrazone-ethyl, chlorflurenol, chlorflurenol-methyl, chloridazon, chlorimuron, chlorimuron-ethyl, chloroacetic acid, chlorotoluron, chlorpropham, chlorsulfuron, chlorthal, chlorthal-dimethyl, cinidon-ethyl, cinmethylin, cinosulfuron, cisanilide, clethodim, clodinafop, clodinafop-propargyl, clomazone, clomeprop, clopyralid, cloransulam, cloransulam-methyl, cyanazine, cycloate, cyclosulfamuron, cycloxydim, cyhalofop, cyhalofop-butyl, 2,4-D, daimuron, dalapon, dazomet, 2,4-DB, desmedipham, dicamba, dichlobenil, dichlorprop, dichlorprop-P, diclofop, diclofop-methyl, diclosulam, difenzoquat, difenzoquat metilsulfate, diflufenican, diflufenzopyr, dimefuron, dimepiperate, dimethachlor, dimethametryn, dimethenamid, dimethenamid-P, dimethipin, dimethylarsinic acid, dinitramine, dinoterb, diphenamid, dipropetryn, diquat, diquat dibromide, dithiopyr, diuron, endothal, EPTC, esprocarb, ethalfluralin, ethametsulfuron, ethametsulfuron-methyl, ethephon, ethofumesate, ethoxyfen, ethoxysulfuron, etobenzanid, fenoxaprop-P, fenoxaprop-P-ethyl, fentrazamide, ferrous sulfate, flamprop-M, flazasulfuron, florasulam, fluazifop, fluazifop-butyl, fluazifop-P, fluazifop-P-butyl, fluazolate, flucarbazone, flucarbazone-sodium, flucetosulfuron, fluchloralin, flufenacet, flufenpyr, flufenpyr-ethyl, flumetralin, flumetsulam, flumiclorac, flumiclorac-pentyl, flumioxazin, flumipropin, fluometuron, fluoroglycofen, fluoroglycofen-ethyl, fluoxaprop, flupoxam, flupropacil, flupropanate, flupyrsulfuron, flupyrsulfuron-methyl-sodium, flurenol, fluridone, flurochloridone, fluroxypyr, flurtamone, fluthiacet, fluthiacet-methyl, fomesafen, foramsulfuron, fosamine, glufosinate, glufosinate-ammonium, glyphosate, halauxifen, halosulfuron, halosulfuron-methyl, haloxyfop, haloxyfop-P, hexazinone, imazamethabenz, imazamethabenz-methyl, imazamox, imazapic, imazapyr, imazaquin, imazethapyr, imazosulfuron, indanofan, indaziflam, iodomethane, iodosulfuron, iodosulfuron-methyl-sodium, ioxynil, isoproturon, isouron, isoxaben, isoxachlortole, isoxaflutole, isoxapyrifop, karbutilate, lactofen, lenacil, linuron, mecoprop, mecoprop-P, mefenacet, mefluidide, mesosulfuron, mesosulfuron-methyl, mesotrione, metam, metamifop, metamitron, metazachlor, methabenzthiazuron, methazole, methylarsonic acid, methyldymron, methyl isothiocyanate, metolachlor, S-metolachlor, metosulam, metoxuron, metribuzin, metsulfuron, metsulfuron-methyl, molinate, monolinuron, naproanilide, napropamide, naptalam, neburon, nicosulfuron, n-methyl glyphosate, nonanoic acid, norflurazon, oleic acid, orbencarb, orthosulfamuron, oryzalin, oxadiargyl, oxadiazon, oxasulfuron, oxaziclomefone, oxyfluorfen, paraquat, paraquat dichloride, pebulate, pendimethalin, penoxsulam, pentachlorophenol, pentanochlor, pentoxazone, pethoxamid, phenmedipham, picloram, picolinafen, pinoxaden, piperophos, pretilachlor, primisulfuron, primisulfuron-methyl, prodiamine, profoxydim, prohexadione-calcium, prometon, prometryn, propachlor, propanil, propaquizafop, propazine, propham, propisochlor, propoxycarbazone, propoxycarbazone-sodium, propyzamide, prosulfocarb, prosulfuron, pyraclonil, pyraflufen, pyraflufen-ethyl, pyrasulfotole, pyrazolynate, pyrazosulfuron, pyrazosulfuron-ethyl, pyrazoxyfen, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-P, rimsulfuron, saflufenacil, sethoxydim, siduron, simazine, simetryn, sodium chlorate, sulcotrione, sulfentrazone, sulfometuron, sulfometuron-methyl, sulfosate, sulfosulfuron, sulfuric acid, tebuthiuron, tefuryltrione, tembotrione, tepraloxydim, terbacil, terbumeton, terbuthylazine, terbutryn, thenylchlor, thiazopyr, thifensulfuron, thiencarbazone, thifensulfuron-methyl, thiobencarb, topramezone, tralkoxydim, tri-allate, triasulfuron, triaziflam, tribenuron, tribenuron-methyl, triclopyr, trietazine, trifloxysulfuron, trifloxysulfuron-sodium, trifluralin, triflusulfuron, triflusulfuron-methyl, trihydroxytriazine, trinexapac-ethyl, tritosulfuron, and [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester; and when the at least one additional pesticide is a herbicide safener, the herbicide safener is selected from the group consisting of: benoxacor, cloquintocet-mexyl, cyprosulfamide, dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxy-benzoyl sulfamoyl)-benzamide, and N-(2-methoxybenzoyl)-4-[(methylaminocarbonyl)amino] benzenesulfonamide.

19. The method of claim 16, wherein the formulation consists essentially of the compound of formula (I).

20. The method of claim 16, wherein the only active ingredient in the formulation is the compound of formula (I).

21. The method of claim 1, wherein the compound of formula (I) is selected from the group consisting of:

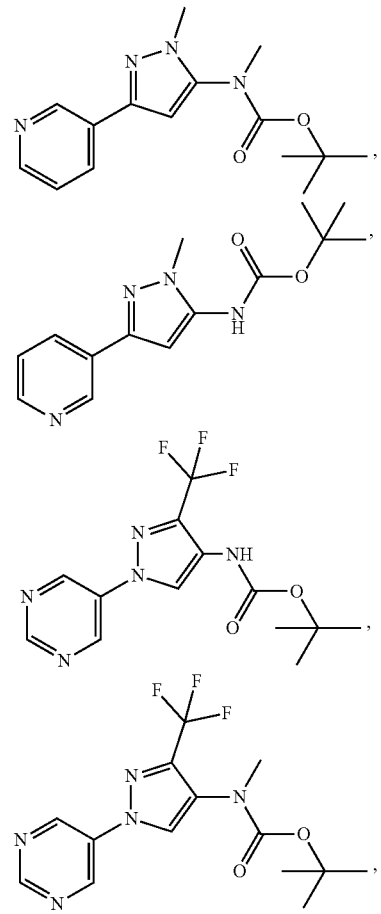

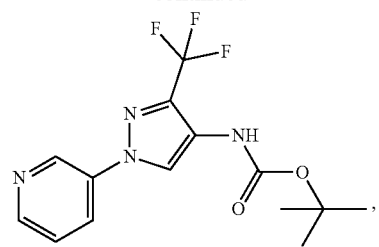
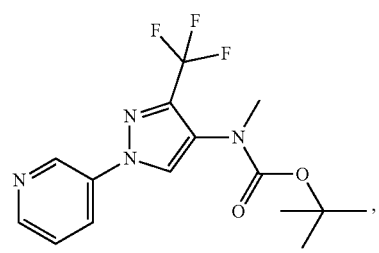
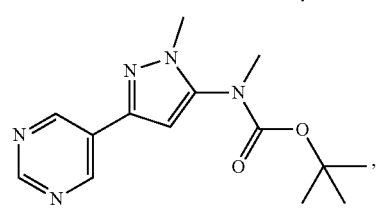
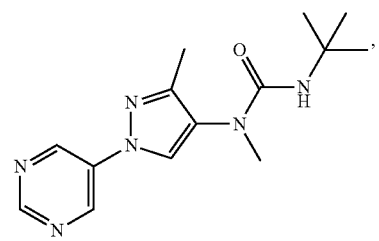
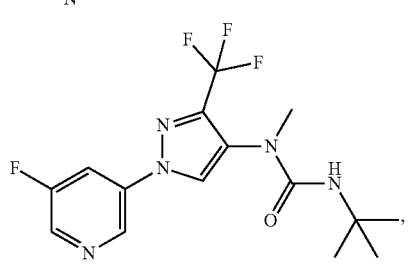
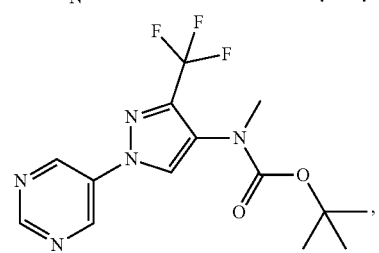
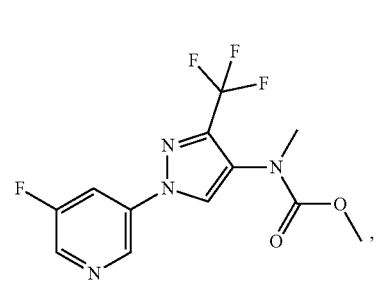
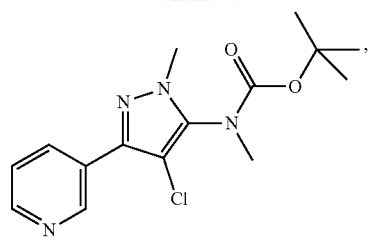
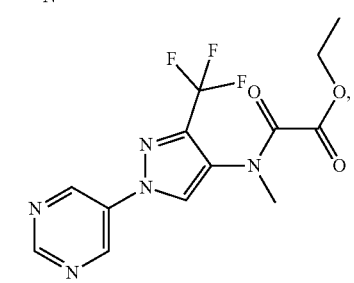
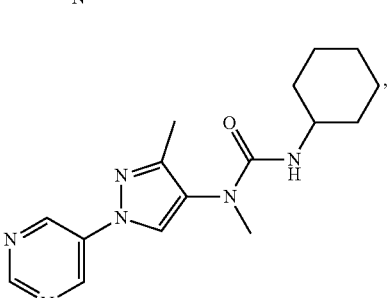
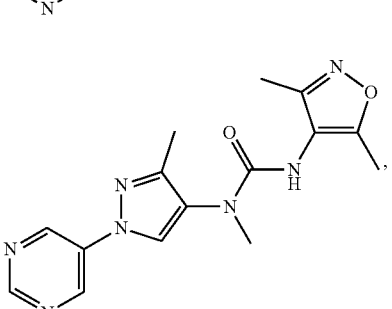
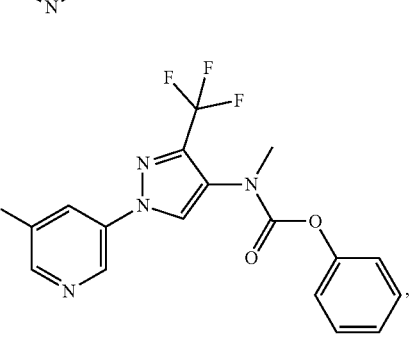
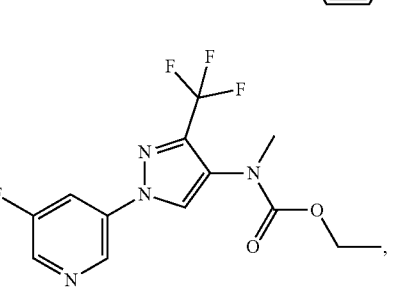

-continued
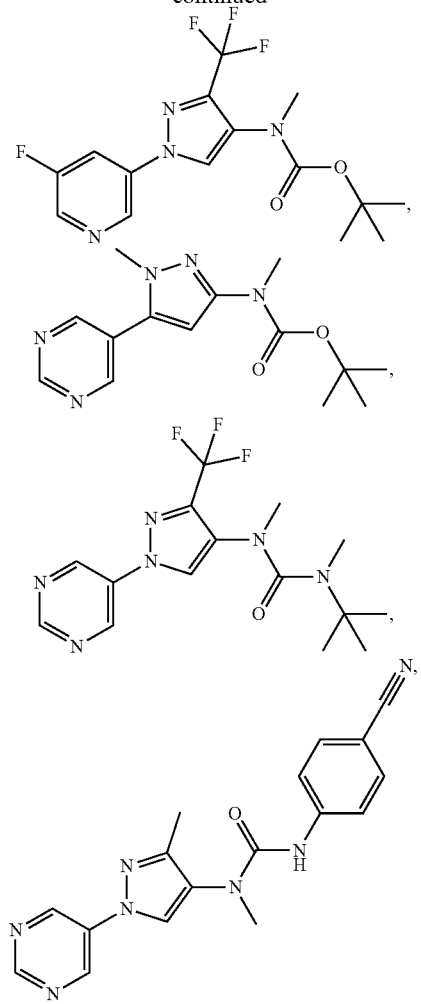
-continued
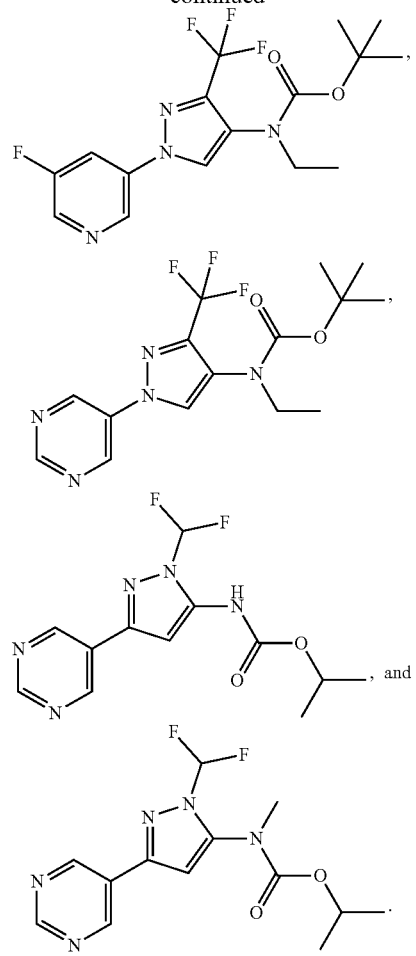
* * * * *